United States Patent
Wilson et al.

(10) Patent No.: US 8,172,189 B2
(45) Date of Patent: May 8, 2012

(54) DEVICE FOR PRECISION POSITIONING OF INSTRUMENTS AT A MRI SCANNER

(75) Inventors: Roger F. Wilson, Sarasota, FL (US); Willet F. Whitmore, III, Longboat Key, FL (US); Bruce Ribble, Swisher, IA (US)

(73) Assignee: CIVCO Medical Instruments Co., Inc., Kalona, IA (US)

( * ) Notice: Subject to any disclaimer, the term of this patent is extended or adjusted under 35 U.S.C. 154(b) by 585 days.

(21) Appl. No.: 12/211,382

(22) Filed: Sep. 16, 2008

(65) Prior Publication Data

US 2009/0072107 A1 Mar. 19, 2009

Related U.S. Application Data

(60) Provisional application No. 60/973,206, filed on Sep. 18, 2007.

(51) Int. Cl.
*A47F 5/00* (2006.01)

(52) U.S. Cl. .................... 248/288.31; 248/314

(58) Field of Classification Search ............. 248/160, 248/276.1, 278.1, 299.1, 484, 481, 181.2, 248/288.31, 314; 600/230, 229, 228, 410, 600/417, 429; 403/90, 114; 285/278, 264, 285/263, 262, 146.1, 282, 145.3, 146.2, 146.3; 606/130, 601; 324/321; 5/601
See application file for complete search history.

(56) References Cited

U.S. PATENT DOCUMENTS

| | | | |
|---|---|---|---|
| 3,584,822 A | | 6/1971 | Oram et al. |
| 3,858,578 A | | 1/1975 | Milo |
| 5,284,130 A | * | 2/1994 | Ratliff .............. 600/229 |
| 5,662,300 A | * | 9/1997 | Michelson ............ 248/279.1 |
| 5,899,425 A | * | 5/1999 | Corey, Jr. et al. ......... 248/276.1 |
| 6,042,155 A | * | 3/2000 | Lockwood .............. 285/264 |
| 6,949,105 B2 | | 9/2005 | Bryan et al. |
| 2003/0086240 A1 | | 5/2003 | Jobs et al. |

(Continued)

FOREIGN PATENT DOCUMENTS

DE   102005023121 A1   11/2003

(Continued)

OTHER PUBLICATIONS

International Search Report re PCT/US2008/076541 dated Jul. 24, 2009.

*Primary Examiner* — Terrell McKinnon
*Assistant Examiner* — Eret McNichols
(74) *Attorney, Agent, or Firm* — Caesar, Rivise, Bernstein, Cohen & Pokotilow, Ltd.

(57) ABSTRACT

A device in the form of an elongated articulating arm having a base for mounting it on or at the MRI apparatus. The free end of the arm is arranged to releasably mount any type of device, e.g., a clamp, a bracket, a biopsy needle guide, etc. The arm includes a plurality of interconnected segments each of which is arranged to pivot about a respective axis perpendicular to the longitudinal axis of the arm, but restricted from twisting about the longitudinal axis. A flexible elongated adjustable tensioning member in the form of plural sections of a cord extend through respective ones of plural flexible sheaths within the arm between the base and the distal end portion to enable the arm to be moved or bent into a desired shape when tension is released and then held in that shape when tension is applied.

19 Claims, 20 Drawing Sheets

U.S. PATENT DOCUMENTS

| | | |
|---|---|---|
| 2004/0149874 A1 | 8/2004 | Stoianovici et al. |
| 2005/0226682 A1* | 10/2005 | Chersky et al. ................. 403/56 |
| 2006/0016006 A1 | 1/2006 | Whitmore, III et al. |
| 2007/0129634 A1* | 6/2007 | Hickey et al. ................. 600/439 |
| 2008/0091170 A1* | 4/2008 | Vargas et al. ................. 604/528 |
| 2009/0121477 A1* | 5/2009 | Pradeilles ................. 285/146.1 |

FOREIGN PATENT DOCUMENTS

| | | |
|---|---|---|
| EP | 0595291 A1 | 5/1994 |
| WO | 2006069288 A2 | 6/2006 |

\* cited by examiner

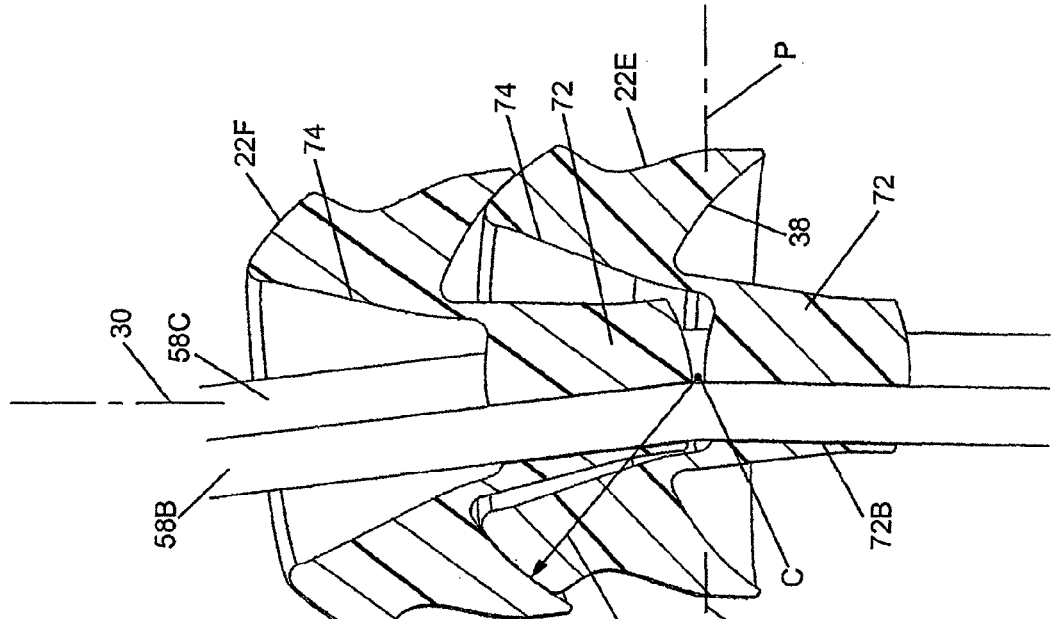
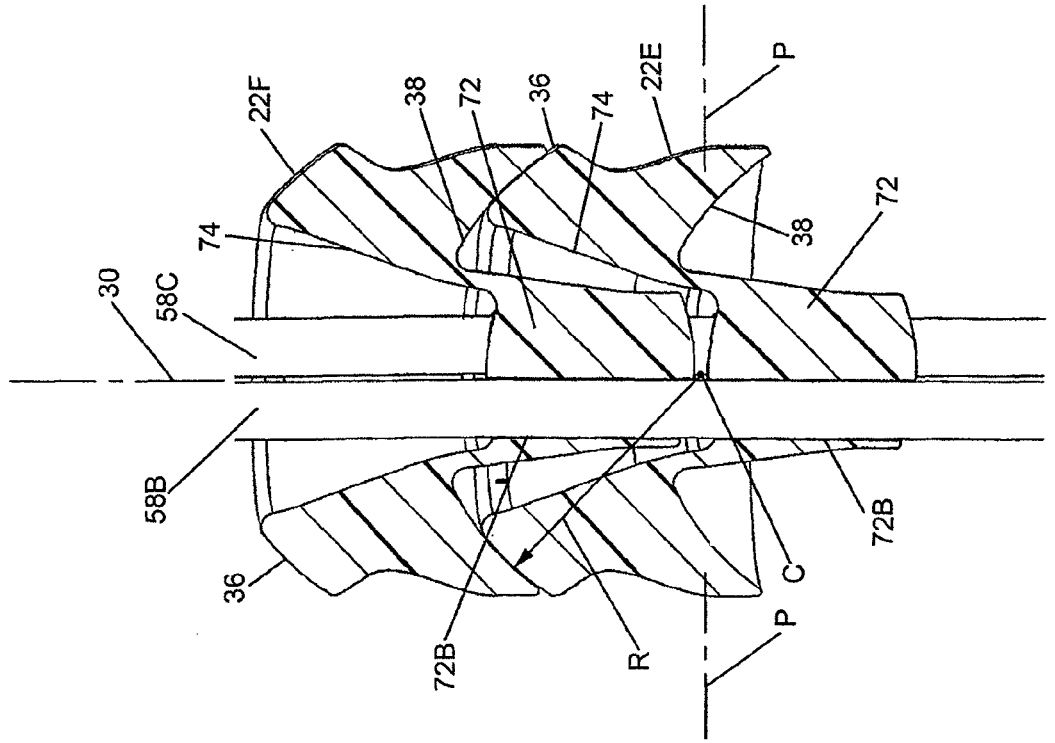

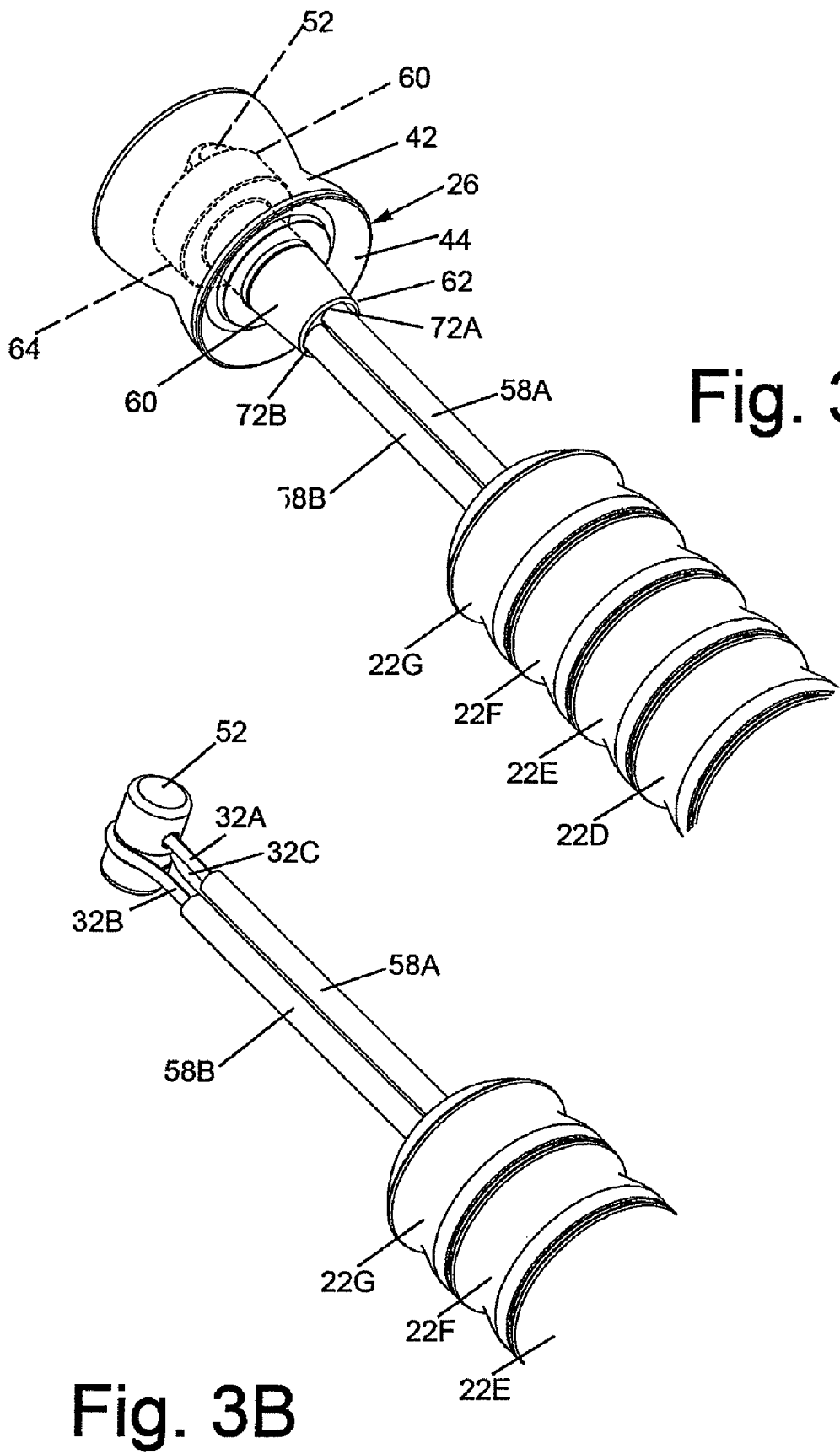

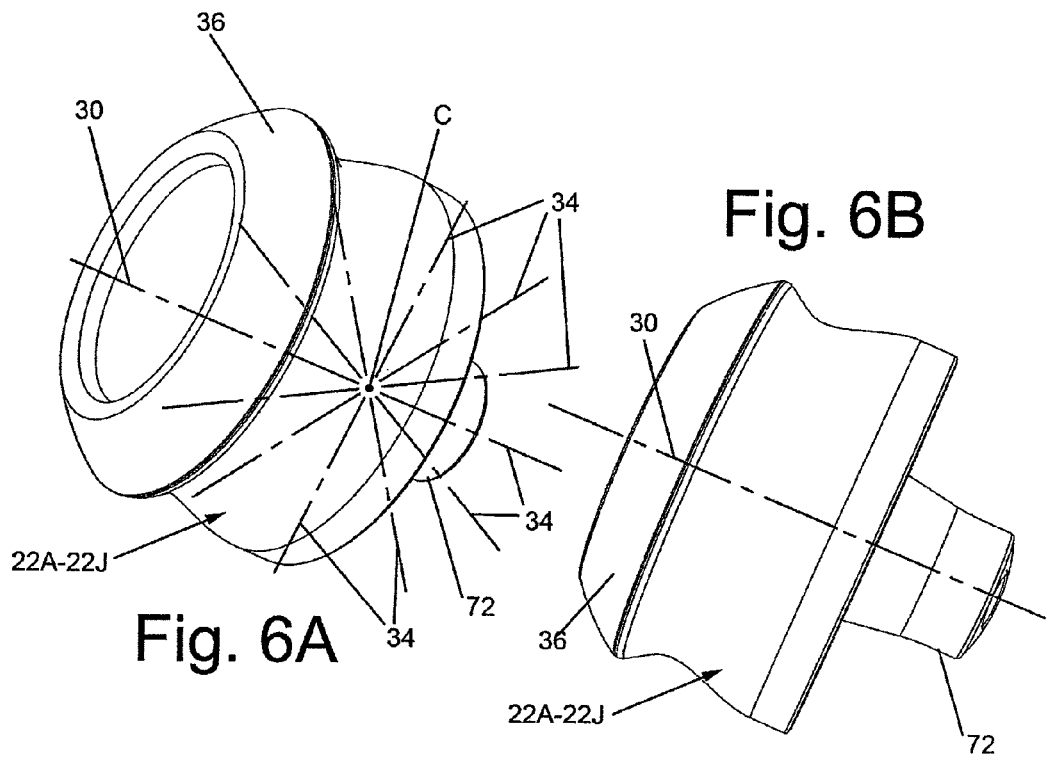
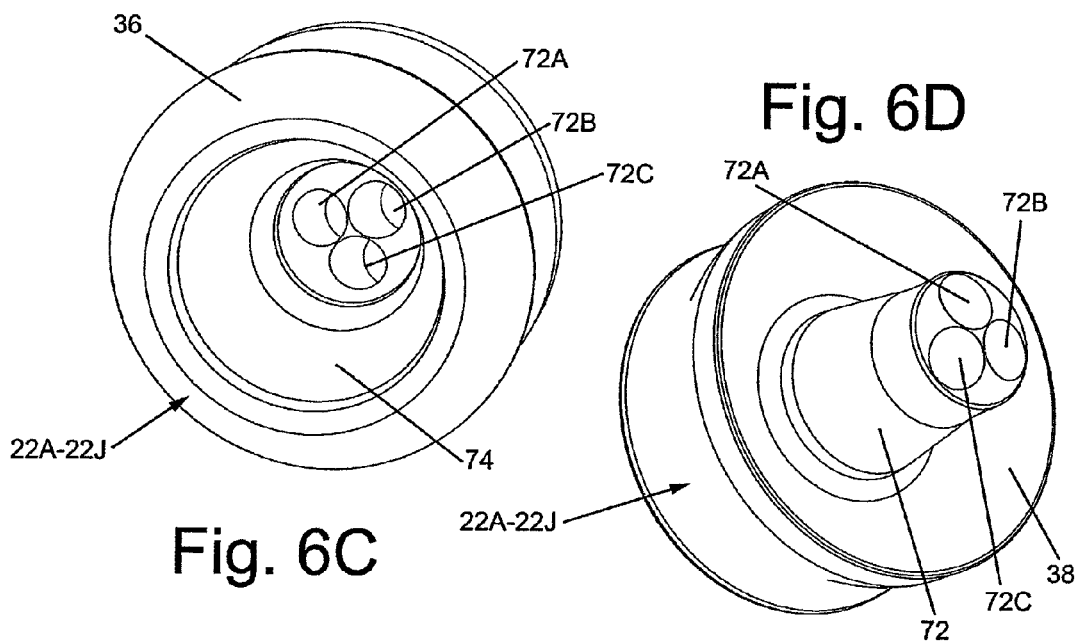

DEVICE FOR PRECISION POSITIONING OF INSTRUMENTS AT A MRI SCANNER

CROSS-REFERENCE TO RELATED APPLICATIONS

This application claims priority from Provisional Application Ser. No. 60/973,206, filed on Sep. 18, 2007, entitled Device for Precision Positioning of Instruments at a MRI Scanner, which application is assigned to the same assignee as this application and whose disclosure is incorporated by reference herein.

STATEMENT REGARDING FEDERALLY SPONSORED RESEARCH OR DEVELOPMENT

"Not Applicable"

INCORPORATION-BY-REFERENCE OF MATERIAL SUBMITTED ON A COMPACT DISK

"Not Applicable"

FIELD OF THE INVENTION

This invention relates generally to holding devices and more particularly for holding devices for use with MRI Scanners.

BACKGROUND OF THE INVENTION

Magnetic Resonance Imaging (MRI) is an advanced technique for visualizing internal human anatomy and disease processes. Its primary use has been for disease diagnosis where its utility in differentiating soft tissue anatomy offers unique visualization characteristics compared to other methods (i.e. CT x-ray, plain X-ray, PET scanning, etc). Recently, the advantages of this unique visualization capability have begun to be applied for targeting and guiding diagnostic biopsies and focal therapies. Because MRI requires a very powerful magnetic field and precise measurements of the molecular movements created by an electromagnetic (radiofrequency) pulse, any distortions that may occur from nearby electrically conductive or magnetic materials will degrade the resulting image data. Therefore, special non-magnetic and non-conductive tools and equipment have been developed by necessity for use in these types of minimally invasive procedures. This set of devices so far includes some surgical instruments, needles, anesthesia equipment, some robotic type devices that use pneumatic powered controls, and the like.

However, many tools and devices that are common to other interventional medical procedures are not available or have yet to be developed for use during MRI. In particular, one such device that is a manually operated mechanical arm for holding a full spectrum of medical devices. The utility of this type of device for holding and positioning medical instruments, guidance devices and other support implements that can remain in a constant spatial relationship to the patient is basic to many invasive medical procedures. The engineering challenges for such a device are not trivial because of the functional requirements that must be met. These include safety and non-interference with the MRI machine, ease of use, sterility, stability, strength, and small axial dimensions because of the very limited space within most MRI scanners. As a consequence, even though there is currently both a need and demand for such a device, nothing that approaches the ideal of meeting these functional requirements has been available until the present invention.

In our copending United States Published Application 2006/0016006 A1, filed Jan. 26, 2006, which is assigned to the same assignee as the subject invention and whose disclosure is incorporated by reference herein there is disclosed and claimed a system is for supporting a patient during computed axial tomography imaging. The system includes a movable platform formed of a radiolucent material, a discrete attachment region in the platform, and a curvilinear articulating arm coupled to the platform at the discrete attachment region. The free end of the arm is arranged to hold any desired medical device, e.g., a clamp, a bracket, or a linear instrument such as a biopsy needle guide, etc. Such devices can be collectively referred to hereinafter as "effectors" (with each particular device being referred to as an "effector"). The patent application also discloses a method for supporting a patient during a plurality of procedures. The method includes: disposing the patient on a movable platform formed of a radiolucent material; positioning a device with respect to the patient, the device being disposed on a curvilinear articulating arm coupled to the platform; placing the platform, positioned device, and patient in a computed axial tomography imaging system and performing an imaging procedure. The curvilinear articulating arm basically includes a central arm having a ball-sleeve arrangement that forms joints to enable the arm to move with six degrees of freedom so that it can be bent into any desired curvilinear shape. To that end, the central arm includes a plurality of sleeves with spherical balls disposed therebetween forming ball and socket connections. In the preferred exemplary embodiment, three balls of a first size are disposed adjacent one another proximate one end of arm, while the remaining balls are of a second size smaller than the first size. Sleeves of a first size and sleeves of a second size smaller than the first size are provided for accommodating the balls of the first size and the second size, respectively, while a transition sleeve is provided, as are intermediate sleeves. The sleeves are configured and dimensioned to receive the balls at ends thereof and thus permit articulating of sleeves with respect to each other. A metal tensioning wire runs generally centrally through sleeves and balls to hold the arm in the shape that it is bent into. One exemplary operation of a wire tensioning mechanism is shown and described in U.S. Pat. No. 3,858,578 (Milo), which is expressly incorporated herein by reference thereto.

In our Provisional Patent Application Ser. No. 60/892,343, filed on Mar. 1, 2007, entitled Device For Positioning Instruments At A Magnetic Resonance Imaging Scanner, which is assigned to the same assignee as this invention and whose disclosure is incorporated herein, there is disclosed and claimed a device for holding an end effector, e.g., a biopsy needle, a clamp, etc., at an MRI apparatus. The device comprises an articulating arm having a proximal end portion, a free distal end portion and a flexible elongated tensioning member located within the arm between the proximal end portion and the distal end portion. The proximal end portion of the arm is in the form of a base arranged to mount the device on or at the MRI apparatus. The free distal end portion of the arm is arranged to mount a desired item thereon (e.g., clamp, a bracket, a biopsy needle guide, etc.). The arm has a longitudinal axis and includes plural segments of non-magnetic and non-conductive material or any material that is magnetic resonance and/or artifact-free. The segments of the arm are arranged to be moved with respect to one another, but are restricted from twisting about the longitudinal axis to enable the arm to be moved into a desired shape and held in that shape when the elongated tensioning member is tensioned.

In accordance with one preferred aspect of the invention of that Provisional Application at least one of the segments is adapted to pivot about a first pivot axis that is perpendicular to the longitudinal axis of the arm and at least one of the segments that is/are immediately adjacent the at least one of the segments is adapted to pivot about a second pivot axis that is perpendicular to the longitudinal axis. The first and second axes are perpendicular to each other. This arrangement precludes the tensioning member from twisting when the arm is moved or bent into its desired orientation.

In accordance with another preferred aspect of the invention of that Provisional Application the tensioning member (e.g., a ribbon like arrangement consisting of an array of plural side-by-side sections or runs of a cord) is mounted within the arm and is actuatable to enable the tension in the elongated tensioning member to be established to hold the arm in the desired shape and to enable the tension in the elongated tensioning member to be released, whereupon the shape of the arm can be changed.

While the holding devices of the prior art may be generally suitable for their intended purposes, they still leave something to be desired from various standpoints. The device of the subject invention addresses those needs.

SUMMARY OF THE INVENTION

In accordance with one aspect of the invention there is provided a device for holding an item adjacent an MRI apparatus. The device basically comprises an articulating arm having a proximal end portion and a free distal end portion and a flexible elongated tensioning member located within the arm between the proximal end portion and the distal end portion. The proximal end portion of the arm is in the form of a base arranged to mount the device on or at the MRI apparatus. The free distal end portion of the arm is arranged to mount a desired item thereon.

The arm comprises plural segments of non-magnetic and non-conductive material or any material that is magnetic resonance and/or artifact-free and has a longitudinal axis. At least one of the segments of the arm has an arcuate concave socket and an immediately adjacent segment has an arcuate convex shoulder surface. The socket of the at least one of the segments receives the shoulder surface of the immediately adjacent segment. The segments are arranged to pivot with respect to each other but are restricted from twisting more than a predetermined angle with respect to each other about the longitudinal axis when the elongated tensioning member is un-tensioned to enable the arm to be moved or bent into a desired shape and held in such shape when the elongated tensioning member is tensioned.

In accordance with a preferred aspect of the invention each of the segments has an arcuate concave socket (e.g., a portion of a spherical concave surface) and an arcuate convex shoulder surface (e.g., a portion of a spherical convex surface). The shoulder surface of one of the segments is received within the socket in the immediately adjacent segment. Furthermore, each of the segments has an aperture in it through which the elongated tensioning member extends.

In accordance with another preferred aspect of the invention each of the segments includes a recess portion located in the shoulder portion and a projection located in the socket. The projection of any one of the segments is located within the recess of the immediately adjacent segment when the shoulder of said immediately adjacent segment is located within the socket of the any one of the segments. This arrangement restricts excess pivoting of the segments with respect to one another.

In accordance with still another aspect of this invention the aperture in each of the segments extends through the recess and the projection of that segment.

In accordance with yet another aspect of this invention the tensioning member comprises at least one run of a cord, the at least one run is disposed generally parallel to the longitudinal axis and extends between the distal end portion and the proximal end portion of the arm.

In accordance with yet another aspect of this invention the arm includes at least at least one sheath through which the cord extends, the sheath being formed of a flexible material resistant to twisting.

In accordance with yet another aspect of the invention there is provided an adaptor device for mounting the arm on a table at or adjacent an MRI apparatus. The table has at least one marginal edge portion. The adaptor device is particularly suited to mount the arm at various longitudinal positions along the table by releasable securement to the table via the at least one marginal edge of the table. In accordance with one preferred embodiment of this aspect of the invention the adaptor device comprises a bridge member having a pair or extensions, each of which is arranged to slidingly engage a respective marginal edge of the table to releasably secure said adaptor at various positions along the table.

DESCRIPTION OF THE DRAWING

FIG. 2A is a longitudinal cross-sectional view of two representative segments of the arm of the holding device of FIG. 2 shown oriented generally linearly, i.e., with their respective longitudinal axes axially aligned with the central longitudinal axis of the arm, whereupon the portion of the arm made up by those two segments is linear;

FIG. 2B is a view similar to FIG. 2A but showing the representative segments pivoted with respect to each other, i.e., with their respective longitudinal axes intersecting each other at an acute angle, whereupon the portion of the arm made up of those two segments is in bent or curved;

FIG. 3A is an isometric view of the distal end portion of the arm with some of the segments of the arm not shown to reveal some interior details of the arm;

FIG. 3B is an isometric view similar to FIG. 3A but with other portions of the arm not shown to reveal other interior details of the arm;

FIG. 6A is a side elevation view of one of the segments of the arm shown in FIGS. 1, 2, 2A and 2B;

FIG. 6B is side elevation view of the segment shown in FIG. 6A;

FIG. 6C is another isometric view of the segment shown in FIG. 6A, but taken from a different angle (from a position closer to the central longitudinal axis of that segment);

FIG. 6D is still another isometric view of the segment shown in FIG. 6A, but taken from a different angle to show the proximal end portion of the segment;

DETAILED DESCRIPTION OF THE PREFERRED EMBODIMENT

Figure 1:
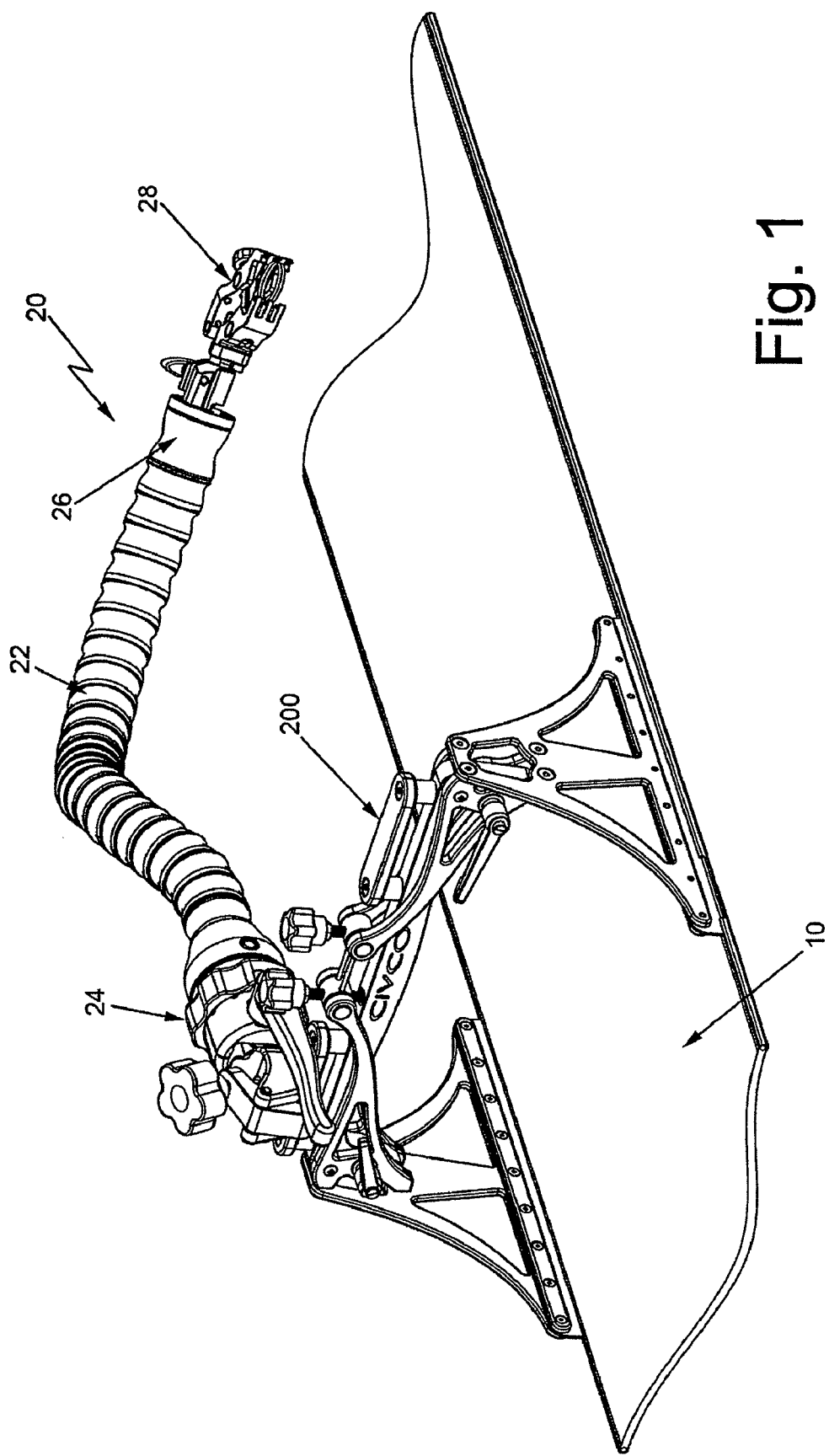
FIG. 1 is an isometric view of a portion of a table to support a patient at a Magnetic Resonance Imaging (MRI) apparatus shown with one exemplary embodiment of a positionable holding device including an arm constructed in accordance with one aspect of the subject invention mounted on that table by use of an exemplary adaptor device also constructed in accordance with another aspect of this invention.

Referring now to the various figures of the drawing wherein like reference characters refer to like parts, there is shown in FIG. 1 a positionable holding device 20 constructed in accordance with one exemplary embodiment of this invention. The device 20 is arranged to be used with any type of magnetic resonance apparatus (e.g., an MRI scanner) or other diagnostic and/or therapeutic apparatus which necessitates the use of non-metallic or magnetic resonance safe adjuncts when in the vicinity of the apparatus. The device is in the form of an elongated arm 22, a base assembly 24 located at the proximal end of the arm and a holding assembly 26 located at the free or distal end of the arm. The base assembly 24 is arranged for manually mounting the device onto any desired structure, e.g., a table 10, of the magnetic resonance apparatus (not shown). The holding assembly 20 is arranged for ready mounting and dismounting (i.e., releasably mounting) any desired end effector 28 on the free end of the arm. Such end effectors may be a clamp, a bracket, a linear instrument such as a biopsy needle guide, etc. or any other device that is to be held in a desired position and orientation with respect to the MRI apparatus. Effectors for use in magnetic resonance environments are typically of non-magnetic, non-conductive plastic materials.

In accordance with one preferred aspect of this invention the components making up its arm are formed of a very stiff and strong material(s), that is/are non-metallic. One particularly suitable material for making up the components of the arm and other portions of the device is Hydlar Z, i.e., a Kevlar reinforced nylon. Other very stiff or rigid materials that provide a very high modulus of flexibility are also contemplated, such as carbon fiber reinforced polymer plastics.

Figure 2:
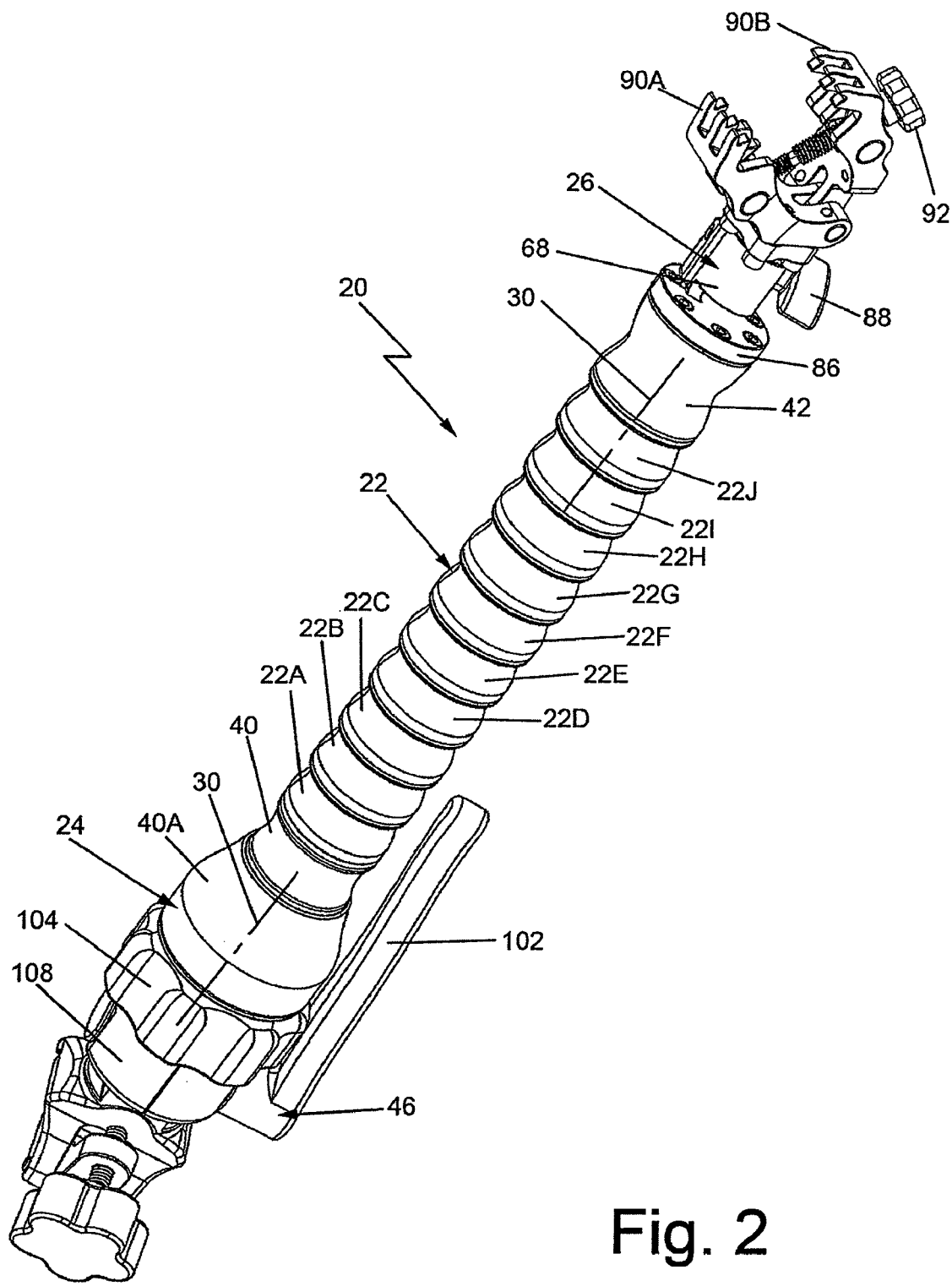
FIG. 2 is an enlarged isometric view of the positionable holding device like that of FIG. 1 but showing its arm having a fewer number of segments than that of FIG. 1.

As best seen in FIGS. 1, 2, 2A, 2B and 4, the arm 22 has a longitudinal central axis 30. That arm is made up of a plurality of similar modular movable links or segments. In the exemplary embodiment shown in FIG. 1 the arm has twenty-four movable segments. In the exemplary embodiment shown in FIG. 2 the arm includes only ten segments, 22 a-22J, in the interest of drawing simplicity. The arms of FIGS. 1 and 2 are exemplary of only two embodiments of an arm constructed in accordance with this invention. Thus, the arm of the holding device 20 of this invention may include many more or less segments than shown in FIGS. 1 and 2. In any case, the segments are identical in construction and are best seen in the various views of FIGS. 2A, 2B, 6A-6D. The views of FIGS. 2A and 2B, show two immediately adjacent or contiguous segments 22E and 22F and how they are interconnected to each other, while FIGS. 6A-6D show only on representative segment of any of the segments 22A-22J.

The segments 22A-22JK are interconnected together and can be moved with respect to one another so that the arm can assume (i.e., be bent into) any desired shape by orienting one or more of the segments with respect to its contiguous (immediately adjacent) segment(s). In order to enable the arm to be bent into the desired shape and then held in that shape the arm includes a elongated tensioning member 32 (FIG. 11). That member will be described in detail later. Suffice it for now to state that in the exemplary embodiment herein it comprises a cable or cord having plural, e.g., three, parallel lines or runs, 32A, 32B and 32C extending through the segments of the arm from the distal end portion of the arm to the proximal and portion. In order to ensure that the elongated tension member doesn't twist about the longitudinal axis 30 of the arm, which twisting could cause the effective internal length of the tensioning member to change (e.g., shorten) and thus adversely affect the accurate and precise positioning of the arm, the arm is constructed such that the segments 22A to 22J cannot twist about the longitudinal axis more than a minimal amount. The minimal amount of twist permitted is a function of various factors, e.g., the amount of pretension on the cable when the arm is initially set up (to be described later), the length of the arm and the number of its segments, etc. Thus, for an exemplary arm like that shown in FIGS. 1 and 2, with a fair amount of pretension the minimum twist between immediately adjacent segments is approximately ten degrees or less.

As will be described later, each of the arm's segments can be pivoted with respect to a contiguous segment about a center point C (FIG. 6A) on the longitudinal axis 30, but is restricted from twisting about the longitudinal axis. In particular, the segments can pivot about any axis 34 (FIG. 6A), hereinafter referred to as a "pivot axis," located in a plane P (FIGS. 2A and 2B) which is perpendicular to the longitudinal axis 30 and which intersects the center point C, but cannot twist about the longitudinal axis more than the minimal amount. This arrangement enables the arm 22 to assume a narrow curvilinear shape that can be contoured to a patient and to fit within the confines of an MRI scanner gantry (typically a round bore). It can also be used in so-called "open" MRI configurations frequently used especially for invasive procedures.

At the distal end of the arm 22, the holding assembly 26 is located. The holding assembly is pivotably connected to the distal end of the distal-most segment 22J and serves as the mount for the end effector 28 on the arm 22. A coupling (to be described later) is located at the proximal end of the arm 22 and serves to pivotably connect the arm to the base assembly 24.

As best seen in FIGS. 2A, 2B, 6A, 6B and 6C each segment 22A-22J includes a curved shoulder 36 at its distal or upper end. The shoulder is convex in shape constitutes an arc of a sphere (ball) of a predetermined radius R, e.g., 29 mm. The lower or proximal end of each segment 22A-22J is in the form of a concave surface or recess 38 of the same predetermined radius as the shoulder 36. As best seen in FIGS. 2A and 2B the proximal or recess surface 38 of the segment 22F is arranged to receive the curved shoulder of the next contiguous segment 22E so that the two segments are pivotally connected together in a ball and socket arrangement. The center point C of that interconnection is located in the plane P (FIGS. 2A and 2B) at the intersection of the various pivot axes 34 and the longitudinal axis 30. Thus, the segments 22F and 22E can pivot about any pivot axis 34 (FIG. 6A) lying in the plane P and intersecting the longitudinal axis 30. Each of the segments of the arm is connected to the next succeeding segment in the same manner as just described with respect to segments 22E and 22F. As will be appreciated by those skilled in the art, the radius of curvature of the shoulder (ball) and socket is selected so that the mating surfaces meet as perpendicular to the longitudinal axis as possible to better manage compression of the material making up the segments. This results in greater holding capacity of the arm.

The proximal-most segment 22A is pivotably connected to a coupling 40 (FIGS. 1, 7, and 11A) forming a portion of the base assembly 24 to pivotably mount the arm 22 on the base assembly. The coupling 40 includes a shoulder (not shown) shaped like the shoulder 36 of the segments 22A-22J. The shoulder of the coupling is received within the arcuate socket 38 of the proximal-most segment 22A, whereupon that segment is arranged to pivot through an arc about the any pivot axis 34 located in the plane P that is perpendicular to the longitudinal axis 30 and which pivot axis extends through the longitudinal axis (i.e., passes through center-point C). The coupling 40 forms a portion of a housing assembly (to be described later). As best seen in FIGS. 1, 9A, 10 and 12 a hollow cover member 40A extends over a portion of the coupling 40.

As also mentioned earlier, the holding assembly 26 is mounted on the upper or distal-most segment 22J of the arm 22. The holding assembly 26 is best seen in FIGS. 2, 3A, 4 and 5 and includes a proximally located mounting member 42 having a curved recess surface 44 (FIG. 3A). The surface 44 is arranged to receive the shoulder 36 of the distal most segment 22J of the arm 22. The mounting member 42 is not keyed to the distal most segment so that when the arm is not heavily tensioned (e.g., locked in position, as will be described later) the mounting member can rotate or twist completely about the longitudinal axis 30 of the arm 22, thereby enabling the end effector 28 mounted thereon to be in any angular orientation with respect to the longitudinal axis 30 (as will be described later).

In order to hold the various segments of the arm 22 together and to the holding assembly 26 and the base assembly 24, the arm 22 includes the heretofore identified tensioning member 32. The tensioning member 32 is located within the interior of the arm and extends through the various segments of the arm. The tensioning member 32 also extends within a portion of the interior of the mounting assembly 26 and within a portion of the base assembly 24. In addition to holding those components together the tensioning member, when tensioned, enables the arm 22 to be fixed or locked in any orientation or shape into which it is placed. When loosened (unlocked) the tensioning member enables the arm to be bent into any other desired shape/orientation and then re-tensioned to re-lock the arm in that new shape/orientation.

As best seen in FIGS. 5, 8, 11A and 11B the tensioning member extends longitudinally through the segments of the arm from the holding assembly 26 to the base assembly 24. A tensioning mechanism 46 (FIGS. 2, 9A-12) is provided as part of the base assembly for applying and releasing tension on the tensioning member. As mentioned earlier, tensioning member 32 is made up of plural loops of a cord (which itself can be a cable made up of multiple strands or can be a monofilament). The cord can be formed of any suitable material exhibiting very low stretch and which is electrically non-conductive. The diameter of the cord can be of an desired size, e.g., (e.g. approximately 2 to 5 mm). Organic or plastic fibers, e.g. aliphatic polymers such as Dyneema and Spectra, aramids, such as Kevlar and Twaron, and organic rod fibers such as PBO and M5, are some examples of appropriate low stretch, high strength fibers that may be used for the tensioning cord. One particularly suitable material for the cord is Vectran, a manufactured fiber spun from a liquid crystal polymer, e.g., an aromatic polyester. Such fibers are noted for thermal stability at high temperatures, high strength and modulus, low creep, and good chemical stability. Moreover, they are moisture resistant and are generally stable in hostile environments.

Figure 5:
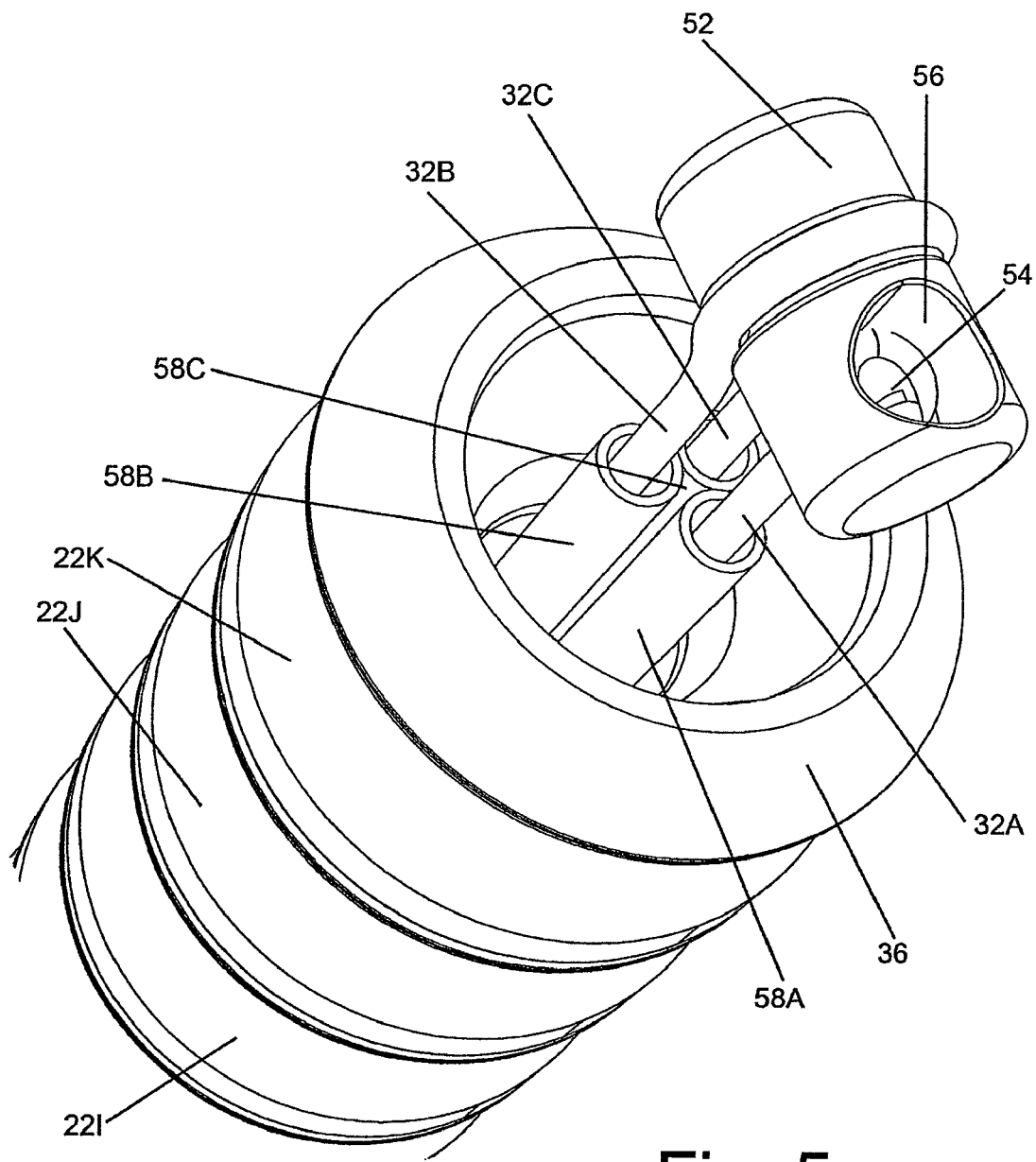
FIG. 5 is an enlarged isometric view of a portion of the arm shown in FIG. 4.

As can best be seen in FIGS. 11A and 11B the cord 32 is arranged so it loops twice about an offset region 48 (to be described later) of a cam shaft 50 (also to be described later) forming a portion of the tensioning mechanism 46 of the base assembly 24. As best seen in FIG. 5, the cord loops once about a pin 52 in the holding assembly 26. The distal end of the cord is in the form of a knot 54 which terminates at a recess 56 within the pin 52. This looped arrangement forms the three cord sections or runs 32A, 32B and 32C. The cord runs are disposed in a side-by-side orientation within the arm 22 to thereby form the triangular array when viewed from a plane intersecting the longitudinal axis 30 as seen in FIG. 5. The cord runs 32A, 32B and 32C are held in this array by the use of respective flexible keying sheaths 58A, 58B and 58C. Each sheath is a thin walled flexible tube that is adapted to receive a respective cord run extending through the length of the sheath. With this arrangement, the length of the tensioning member 32 is consistent irrespective of how much one bends the arm 22. In particular, the construction of the segments 22A-22J (to be described hereinafter) and the use of the sheaths 58A, 58B and 58C keys the segments together and thus prevents twisting of the segments about the longitudinal axis to ensure that the distance between interior surface contact surfaces of the tensioning cord does not change with arm segment angulation (pivoting).

As mentioned earlier the mounting member 42 is enabled to twist about the longitudinal axis of the arm to enable the end effector 28 to be in any angular orientation with respect to that axis. To that end as best seen in FIG. 3A the interior of the mounting member 42 includes a symmetrical cavity located centered on the longitudinal axis of the arm and in which a correspondingly shaped pin holder 60 is disposed. The pin holder 60 is keyed to the distal most segment 22J of the arm by virtue of the keying sheaths 58A, 58B and 58C (as will be described later) so that it cannot rotate with respect to that segment. The pin holder 60 includes a male projecting portion 62 having respective parallelly oriented apertures through which the three sheaths 58A, 58B and 58C and their respective cord runs 32A, 32B and 32C pass. The distal end 64 of the pin holder 60 is in the form of a flange whose upper surface includes a diagonally oriented groove. The pin 52 is disposed in the groove. As mentioned earlier, the knot 54 at the distally located free end of the cord 32 is disposed in a bore 56 in the pin 52, with the contiguous portion of the run 32A of the cord extending through an aperture in communication with that bore. From there the cord run 32A extends down (proximally) through the sheath 58A in the arm to the base assembly 24 from which the next run 32B of the cord extends back (distally) through the sheath 58B in the arm to the pin 52. That cord run then loops about the pin 52 as clearly shown in FIGS. 3B and 5, from whence the next cord run 32C extends down (proximally) through the sheath 58C in the arm to the base assembly where it terminates at a clip 66 (FIGS. 11A and 11B) which will be described later. Thus, when tension on the tensioning member in the arm is relaxed the holding assembly 26 is enabled to twist about the longitudinal axis of the arm, while the pin holder, the sheaths 58A, 58B and 58 and the cord runs 32A, 32B and 32C, respectively, remain stationary with respect to all of the segments of the arm.

Other details of the holding assembly 26 will be described later. Suffice it for now to state that it includes a clamp portion 68 (FIGS. 2 and 4) having a slotted throat 70 in which a portion of the end effector 28 can be inserted for releasable securement to the holding assembly.

Referring now to FIGS. 2A and 2B more details about the construction of the segments 22A-22J of the arm will now be described. As can be seen each segment includes a male projecting member 72 extending along the longitudinal axis 30 from the center of the socket 38 and a correspondingly shaped female recess 74 extending along the longitudinal axis from the center of the shoulder 36. As best seen in FIGS. 6C and 6D three apertures or passageways 72A, 72B and 72C extend parallel to each other and to the longitudinal axis between the bottom of the recess 74 of one segment and the free end of the projection 72 of that segment. These apertures are arranged to receive respective ones of the sheaths 58A, 58B and 58C. The male projection 72 of one segment is adapted to be received within the female recess 74 in the immediately adjacent segment.

As will be appreciated by those skilled in the art the parallel extending sheaths, which extend throughout the entire length of the arm (e.g., pass through the apertures or passageways in each of the segments), effectively key the arm's segments together to prevent their twisting with respect to each other about the longitudinal axis beyond a minimal degree of permitted twist.

As best seen in FIGS. 2A and 2B, the depth of the recess and the length the projection is such that when the two segments are interconnected as shown a small gap results between the proximal end of the projection and the distal end of the cooperating recess. This gap is located at approximately the center point C of the ball and socket joint created between those two segments. Thus, when the sheaths are extended through the apertures 72A, 72B and 72C the portion of each sheath located in the gap between immediately adjacent segments will be located at approximately the center point or pivot point of those segments, thereby enabling the segments to pivot with respect to each other about any pivot axis 34 extending through the center point C. Moreover, by virtue of the gap being as small as possible the sheaths are resistant to twist (the primary forces on the sheaths are shear). Further still, the geometry of the segments are configured to minimize segment movement of alignment shift when locking the arm (i.e., tensioning its tensioning member). The coupling 40 includes a recess shaped like the recess 74 of each of the segments 22A-22J, to receive the projection 72 of the proximal-most segment 22A to enable that segment to pivot with respect to the coupling 40 in the same manner as any other segment can pivot with respect to its immediately adjacent segment. As best seen in FIG. 3A the projection 62 of the pin holder 60 is correspondingly shaped to the recess 74 in the distal-most segment 22J to effect the connection between the mounting member and that arm segment.

It should be pointed out at this juncture that a common sheath (not shown) of non-circular (e.g., square, triangular, pentagonal, etc.) cross section for receipt of the parallel runs of the cord can be utilized in lieu of the separate circular sheaths 58A-58C described above, with the common sheath extending through a correspondingly shaped aperture in each of the segments to ensure that the sheath does not twist with respect to the segment through which it passes.

It also should be pointed out that while in the exemplary preferred embodiment described herein the tensioning member 32 is made of an array of three cord sections 32A, 32B and 32C, it is contemplated that it can be formed of any number of cord sections. In fact, it the tensioning member can consist of a single cord section or run, providing that the single run can sustain sufficient tension to hold the arm in position once it is bent into the desired orientation and providing that the arm is constructed so that its segments do not twist with respect to each other to prevent twisting of the single run cord.

Figure 11A:
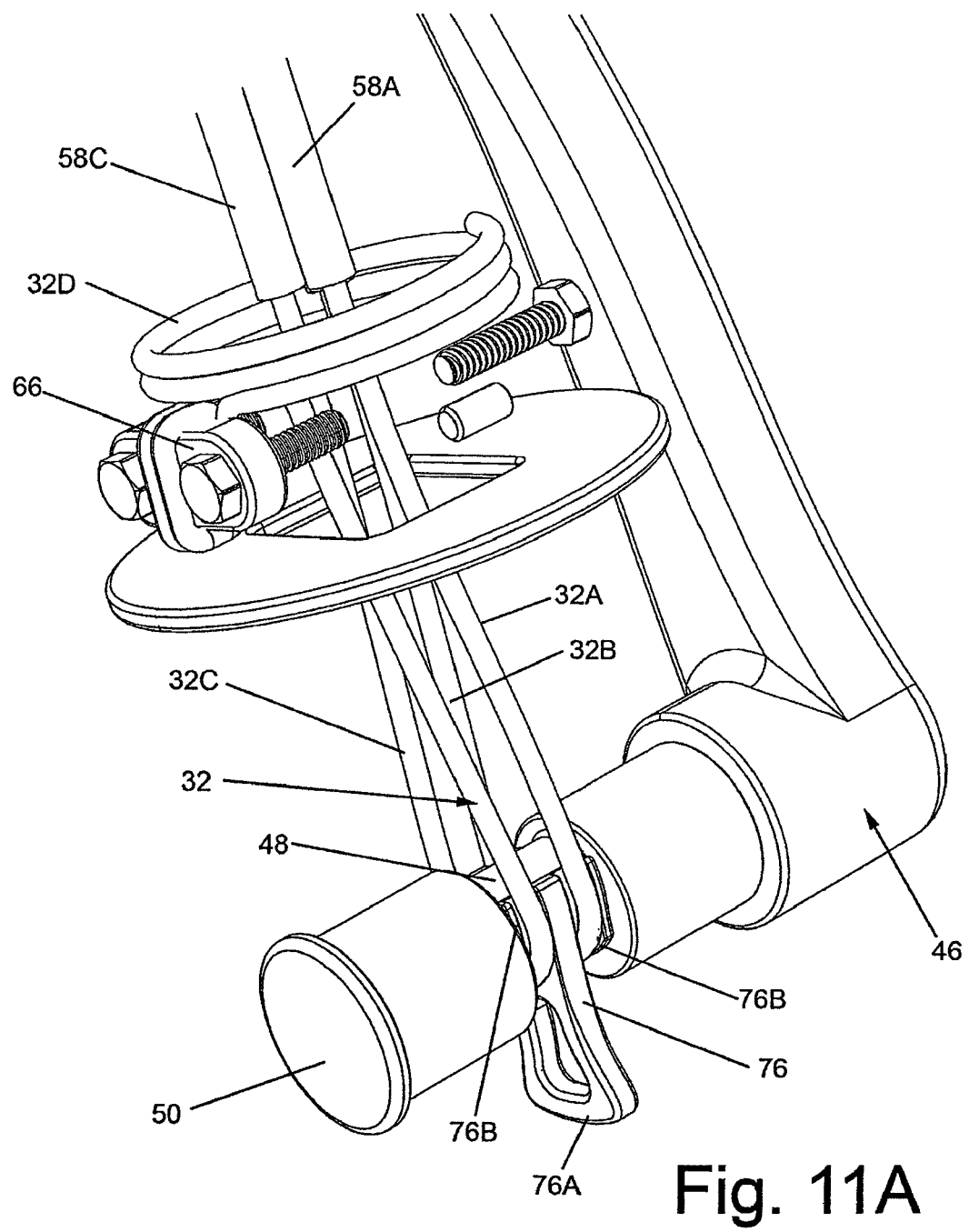
FIG. 11A is another isometric view of the portion of the base assembly shown in FIG. 10, but taken from a different angle and with other portions of the holding device not shown to reveal some of the interior details of the device.
Figure 11B:
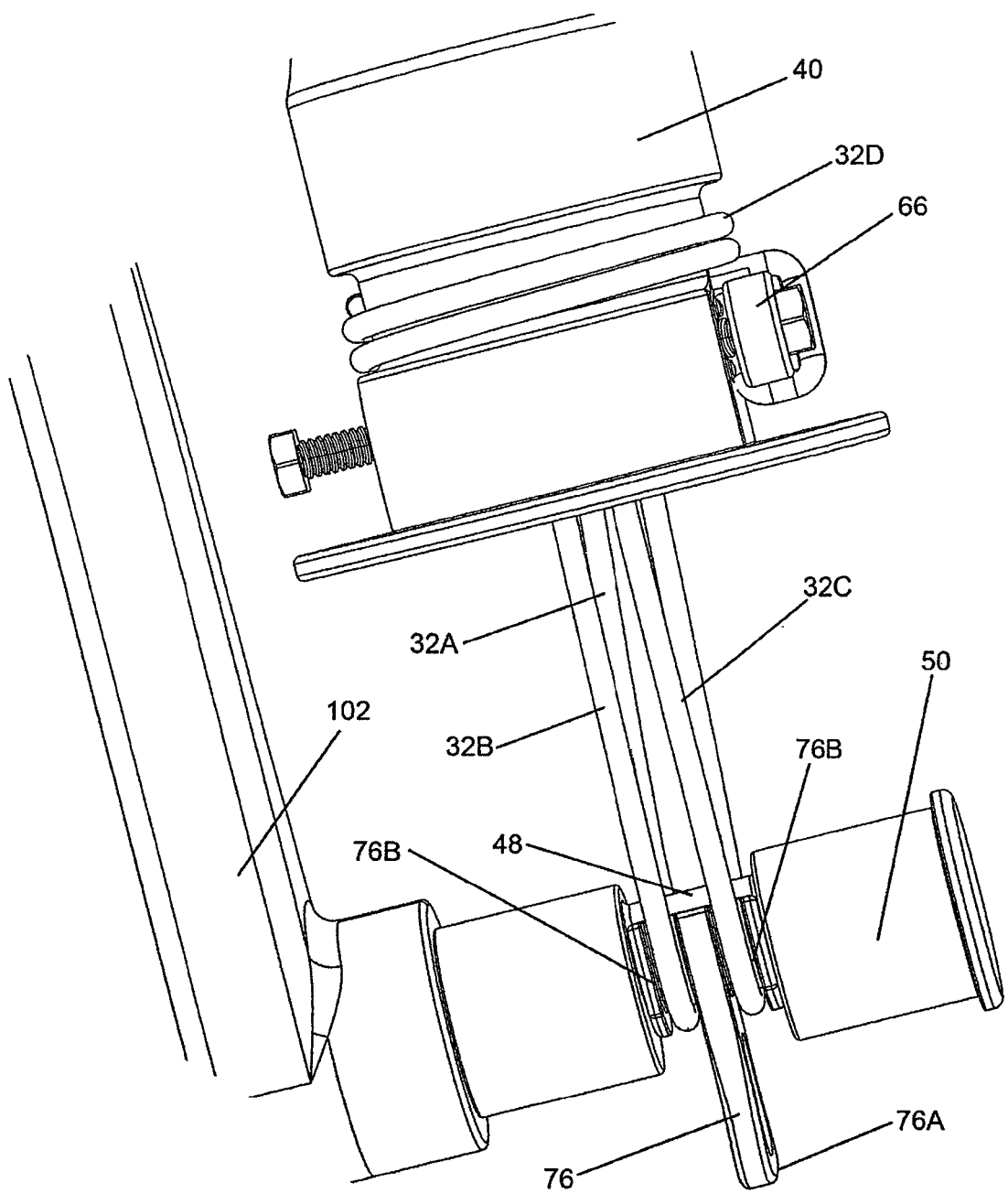
FIG. 11B is plan view of a portion of the base assembly shown in FIG. 10, but taken from a different angle and with other portions of the holding device not shown to reveal some of the interior details of the device.

As best seen in FIG. 11A, in order to secure the cord to the base assembly 24 and to enable the tensioning of the cord, the two loops at the proximally located end portion of the cord extends about the offset portion 48 of the cam shaft 50 of the tensioning mechanism 46. In particular, these loops pass around a guide 76. The guide 76 is a member that is pivotably mounted on the offset portion 58 of the cam shaft and includes a pair of spaced grooves, each arranged to hold a respective loop of the cord. The cord 32 passes from the guide 76 to the heretofore identified clip 66. That clip is in the form of a clamp that is bolted to a housing member 78 forming a portion of the housing assembly of the base assembly 26.

Figure 7:
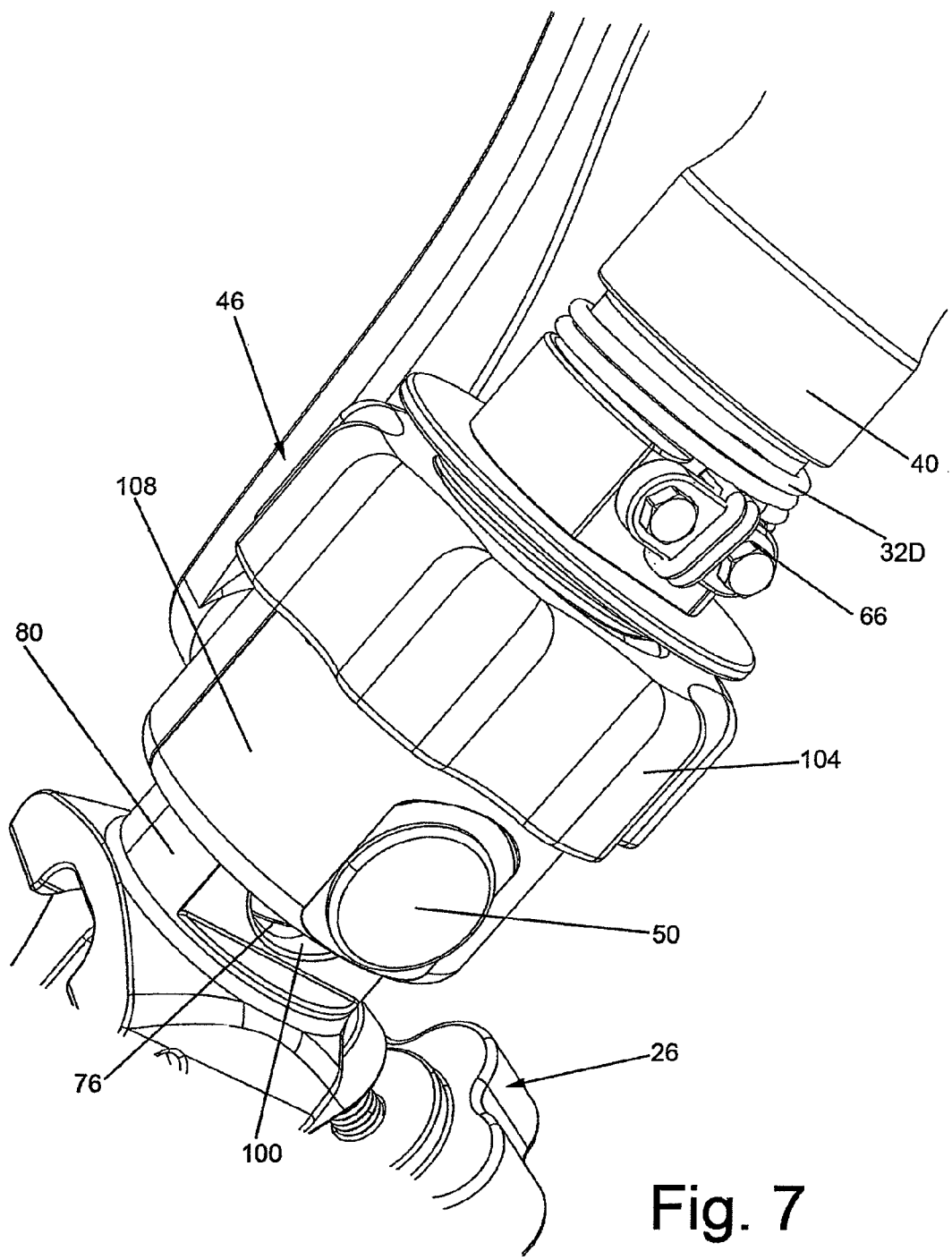
FIG. 7 is an isometric view of a portion of the base assembly making up the positionable holding device of FIGS. 1 and 2, with a portion of the holding device not shown to reveal some of the interior details of the device.

The housing assembly basically comprises a housing member 80 (FIG. 9B) and the heretofore identified coupling 40. The housing member 80 includes a block 82 at its upper end for receipt within a correspondingly shaped cavity in the proximal end of the coupling 40 to fixedly secure them together. The coupling 40 includes a cylindrical portion just above the block 82 about which the free end portion 32D of the cord 32 is wrapped as shown in FIG. 7. That free end portion 32D is the portion of the cord 32 that is manually pulled to pretension the cable upon initial assembly of the device 20 (as will be described later).

Figure 4:
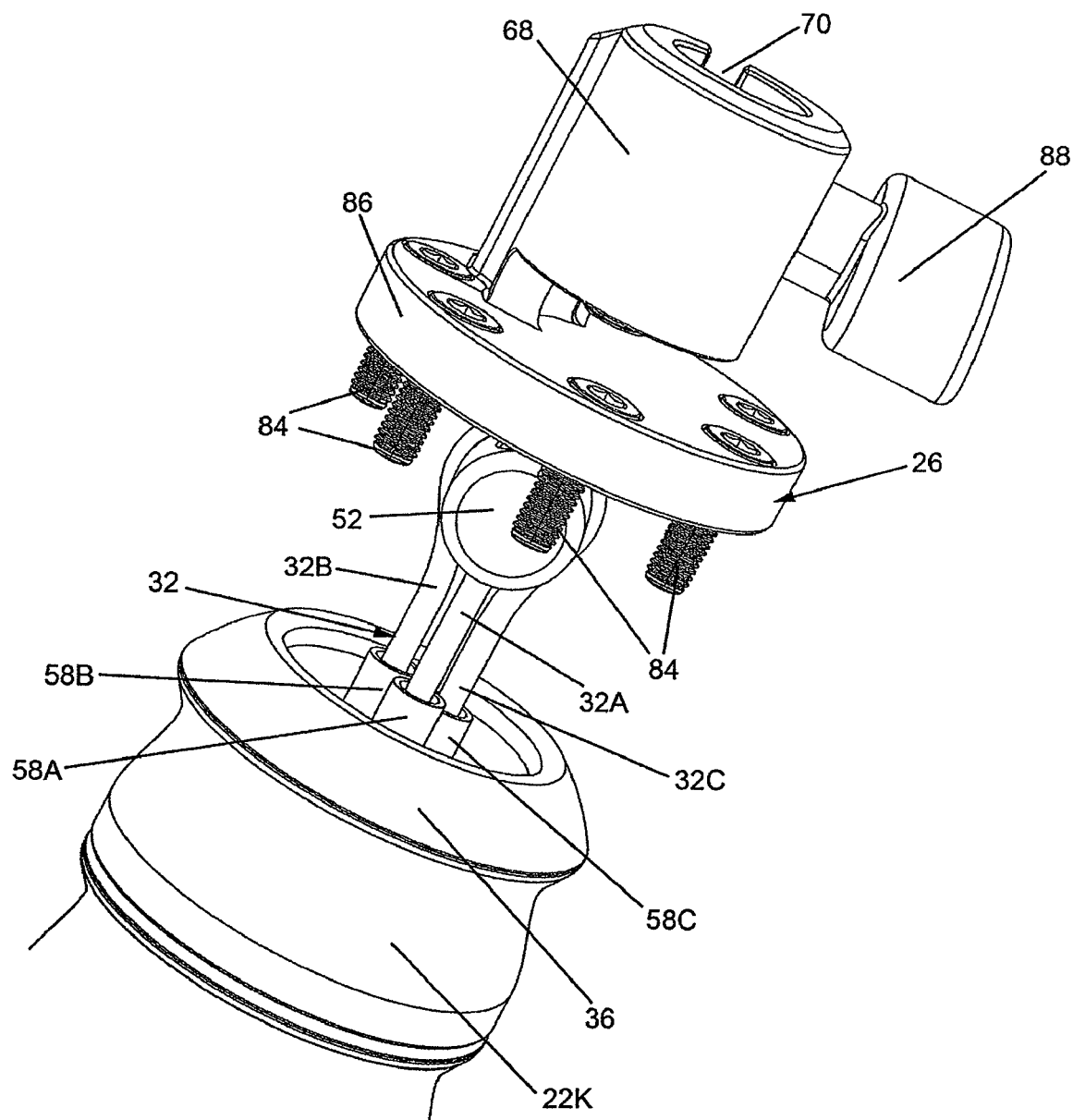
FIG. 4 is an enlarged isometric view of the free or distal end of the positionable holding device shown in FIGS. 1 and 2 with some portions not shown to reveal interior details of the device.

Turning now to FIGS. 2 and 4 the details of the mounting assembly 26 will now be discussed. This assembly basically comprises the mounting member 42, plural screws 84 and the clamp portion 68 having a slotted throat 70. The clamp portion is in the form of a circular plate 86 having clearance holes through which the screws 84 extend to fixedly secure the clamp portion to the mounting member 42. The slotted throat 70 of the clamp portion projects distal from the plate 86 to form the distal end portion of the assembly 26. The interior or throat of the clamp portion 68 is arranged to receive a pin (to be described shortly) forming a portion of the end effector 28. A partially threaded thumbscrew or bolt 88 extends through portions of the collar contiguous with the slotted throat. The thumbscrew includes a handle 88 at its free end for tightening the thumbscrew and thereby bringing the collar portions contiguous with the throat towards each other to reduce the diameter of the slotted throat.

The exemplary end effector 28 shown herein basically comprises a clamp in the form of a pair of opposed jaws 90A and 90B which are pivotably connected together and mounted on a base plate by means of plural bolts. The base plate includes the heretofore mentioned pin projecting downward from the base plate. In order to effect the opening/closing and tightening of the jaws a partially threaded bolt 92 having a portion with a right-hand thread and a left hand thread is provided, with the threads engaging respective pivotable members in the respective jaws. The bolt includes a knob on its free end to tighten or loosen the bolt. The releasable mounting of the end effector 28 onto the arm 22 can be readily accomplished by loosening the bolt 88 of the clamp to open its slotted throat, whereupon the pin of the end effector's mounting plate can be inserted therein. The bolt can then be tightened by means of the rotation of its handle, thereby securing the end effector onto the arm 22.

As mentioned earlier other types of end effectors can be used on the device 20. To that end, such other end effectors should include some mounting plate, like that of the exemplary embodiment herein, or at least a pin shaped and sized to be inserted into the slotted throat of the clamp. Irrespective of the type of end effector utilized, since the diameter of the slotted throat of the holding assembly 26 is adjustable by virtue of the thumbscrew, the holding assembly may allow axial rotation of the end effector 28 with respect to the arm or may lock the end effector against axial rotation, as required by the operator.

Turning now to FIGS. 2 and 7-12 further details of the base assembly 24 will now be described. As mentioned earlier this assembly enables the arm to be mounted on any desired structure. If the structure includes an edge portion, e.g., a rail or bar extending along a side of the table, the arm may be mounted directly thereon via a clamp mechanism (to be described later) of the base assembly. If the structure onto which the arm is to be mounted does not include a rail or bar or some other portion to which the clamp assembly can be releasably secured, an adaptor device 200 constituting another aspect of this invention may be provided. The adaptor device 200 will be described later in connection with use of a table like that shown in FIGS. 1, 14 and 15.

The base assembly 24 enables a user to readily secure the device 20 to the table on which the patient is placed, or to an object that is fixed to the patient that remains in constant relation to the patient or the procedural site for the duration of a procedure. The arm can have an appropriate end effector attached and may be covered with a sterile drape or sleeve. It may then be brought in to the procedure field at an appropriate time and manually attached to a medical instrument and positioned appropriately, and then locked in position for as long as required.

The means for mounting the base assembly 24 of the positioning device 20 onto a rail of a patient table may come in two or more configurations (e.g., mounting to a standard flat-bar type medical table rail), or mounting to a round or rectangular bar, or a table edge, etc. (not shown). In fact, it is contemplated that the base assembly can be configured to releasably secure it to any type of structure. In the exemplary embodiment shown, the base assembly 24 includes a clamp mechanism best seen in FIG. 12 for releasably securing the device 20 at any longitudinal position along the rail of the patient support table or to a portion of the adaptor device 200 (as will be described later). That clamp mechanism basically comprises a fixed jaw 94A forming a portion of a housing member 80 of the base assembly and a movable jaw 94B. The movable jaw is pivotably connected to the fixed jaw by a hinge pin 96. Each of the jaws includes a free end, with the free ends of the jaws being opposed to each other to form a throat which is arranged to be opened for receipt of the rail of the table or some other suitably shaped structure. A threaded bolt 98 extends through the jaws and terminates at its free end in a knob 98A. Tightening of the knob 98A brings the free end of the movable jaw towards the free end of the fixed jaw to reduce the size of the throat, thereby clamping the rail of the table in the throat. The jaws can be readily released, such as would be desired in order to move the device 20 to a different longitudinal position along the table, by turning the knob 98A in the appropriate direction.

Figure 10:
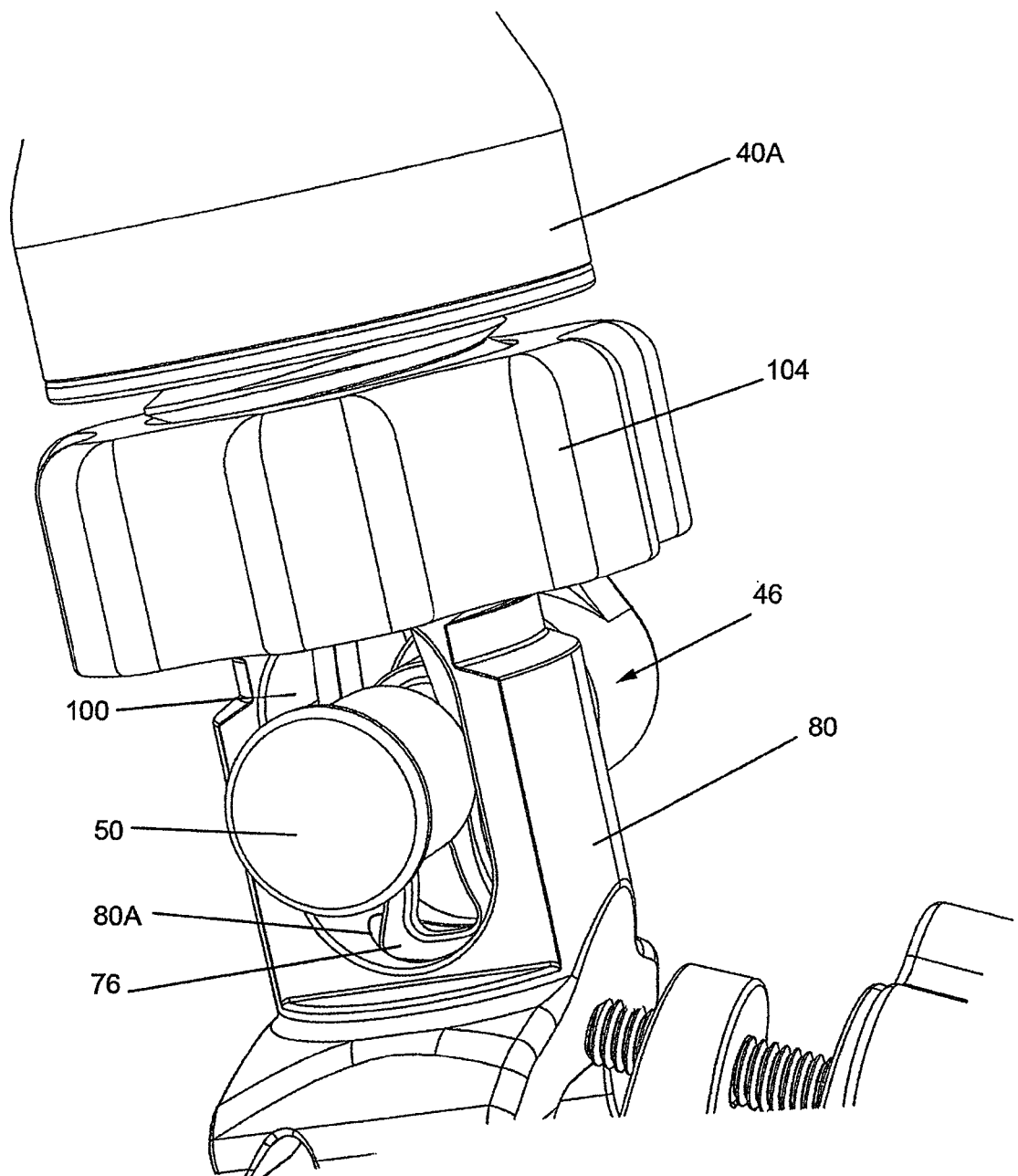
FIG. 10 is another isometric view of the portion of the base assembly shown in FIG. 9A, but taken from a different angle and with other portions of the holding device not shown to reveal some of the interior details of the device.
Figure 12:
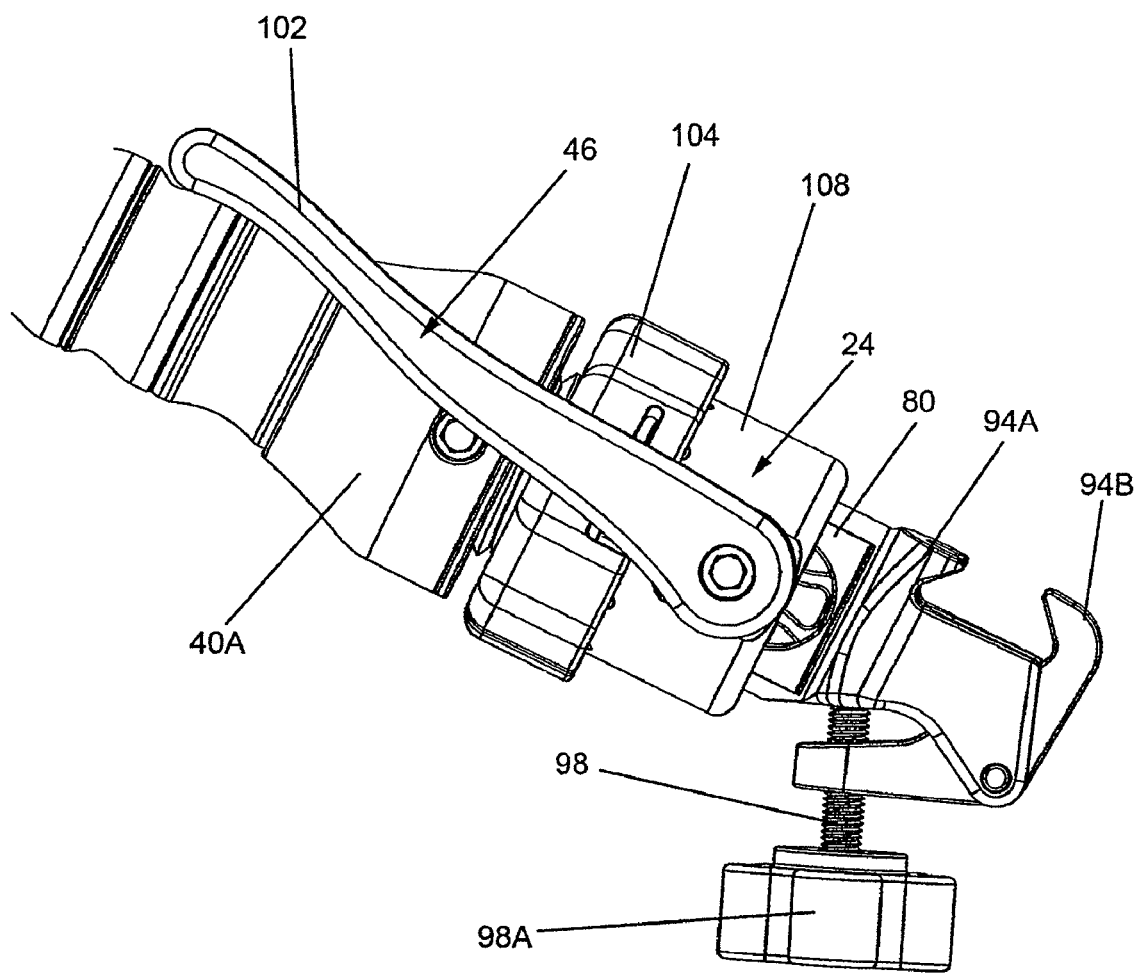
FIG. 12 is a side elevation view of the clamp portion of the base assembly of the holding device of FIGS. 1 and 2.

The details of the mechanism of the base assembly 24 for tensioning the tensioning cord 32 will now be discussed with reference to FIGS. 8-11B. To that end, the base assembly 24 includes the heretofore identified housing member 80. The housing member 80 includes a transversely extending passageway or slot 100 through which the heretofore identified cam shaft 50 extends. A lever 102 is fixedly secured to one end of the cam shaft. The cam shaft is a cylindrical rod of circular cross-section. The center region of the cam shaft includes a portion that is undercut, i.e., is of circular cross section but its center is offset from the rotation axis of the cam shaft. This undercut offset portion forms the heretofore identified offset region 48. As best seen in FIGS. 10-12 the guide 76 is located on the offset region of the cam shaft. The guide 76 includes a projecting portion 76A (whose function will be described later) and a pair of grooves 76B on opposite sides of the projecting portion 76A. The primary function of the guide 76 is to act as a bushing between the cord 34 and the offset portion 48 of the cam shaft 50. To that end the two looped ends of the cord 32 extend about respective grooves 76B of the guide 76 so that those looped ends are located in the offset region 48 of the cam shaft 50 to secure one end of the cord forming the tensioning member thereto. As mentioned earlier other sequential portions of the cord are looped about this offset region 48 and about the pin 52 in the holding assembly 26 to form the tensioning assembly. The free end of the guide's projecting portion 76A is arranged to be located in a bore 80A in the housing member 80 (FIG. 10). The bore 80A is in communication with the slot 100 through which the cam shaft 50 passes to hold the guide 76 on the cam shaft and keep the guide from rotating and coming off.

The tightening or loosening of the tensioning cord 32 is readily effected by pivoting the lever 102 in the appropriate direction to bring the offset portion 48 of the cam shaft 50 and the cable guide 76 mounted thereon either closer or further from the pin 52 at the distal end of the arm 22 and over which the tensioning cord is looped.

Figure 8:
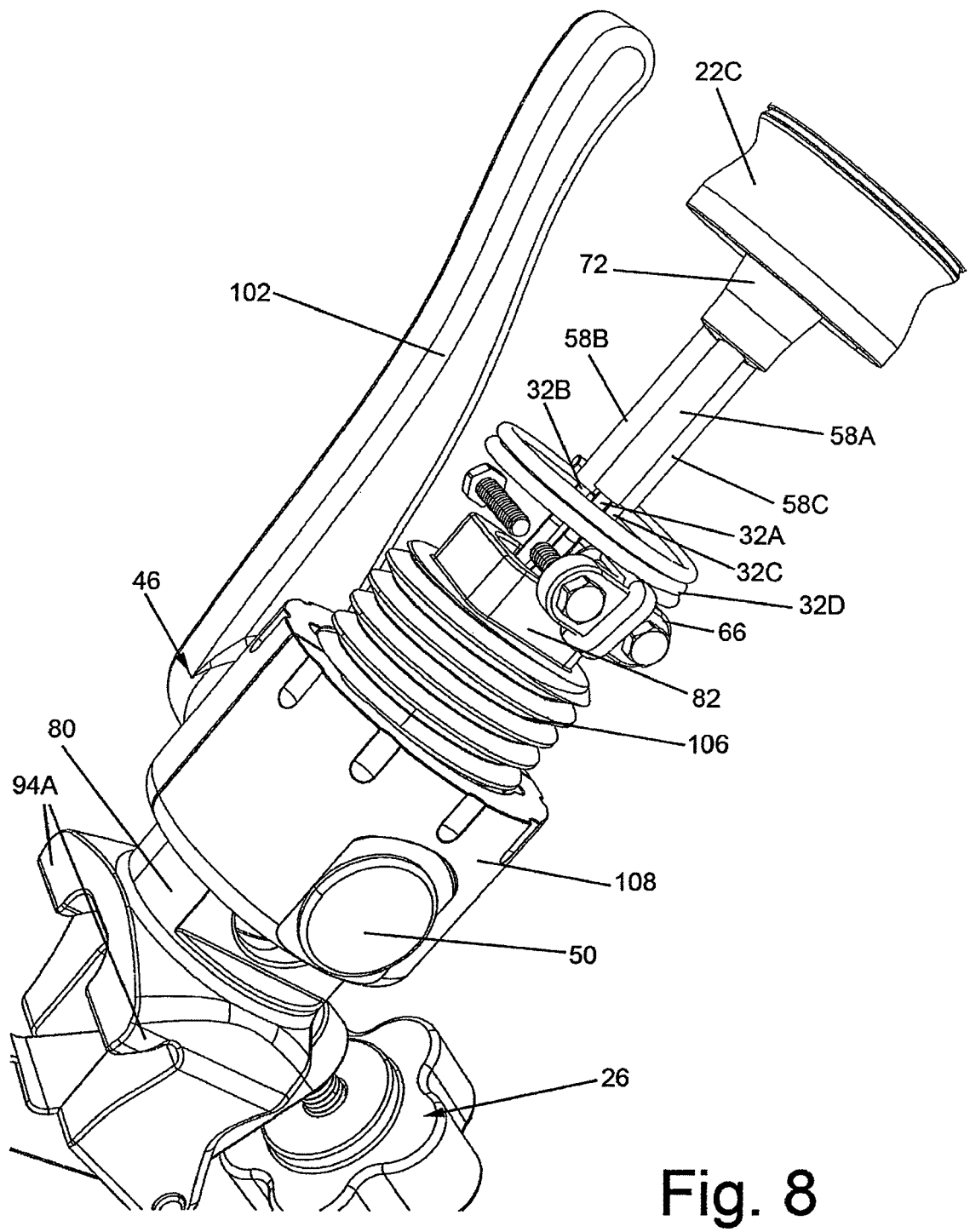
FIG. 8 is another isometric view (slightly reduced in size as compared to FIG. 7) of a portion of the base assembly making up the positionable holding device of FIGS. 1 and 2, with other portions of the holding device not shown to reveal some of the interior details of the device.
Figure 9A:
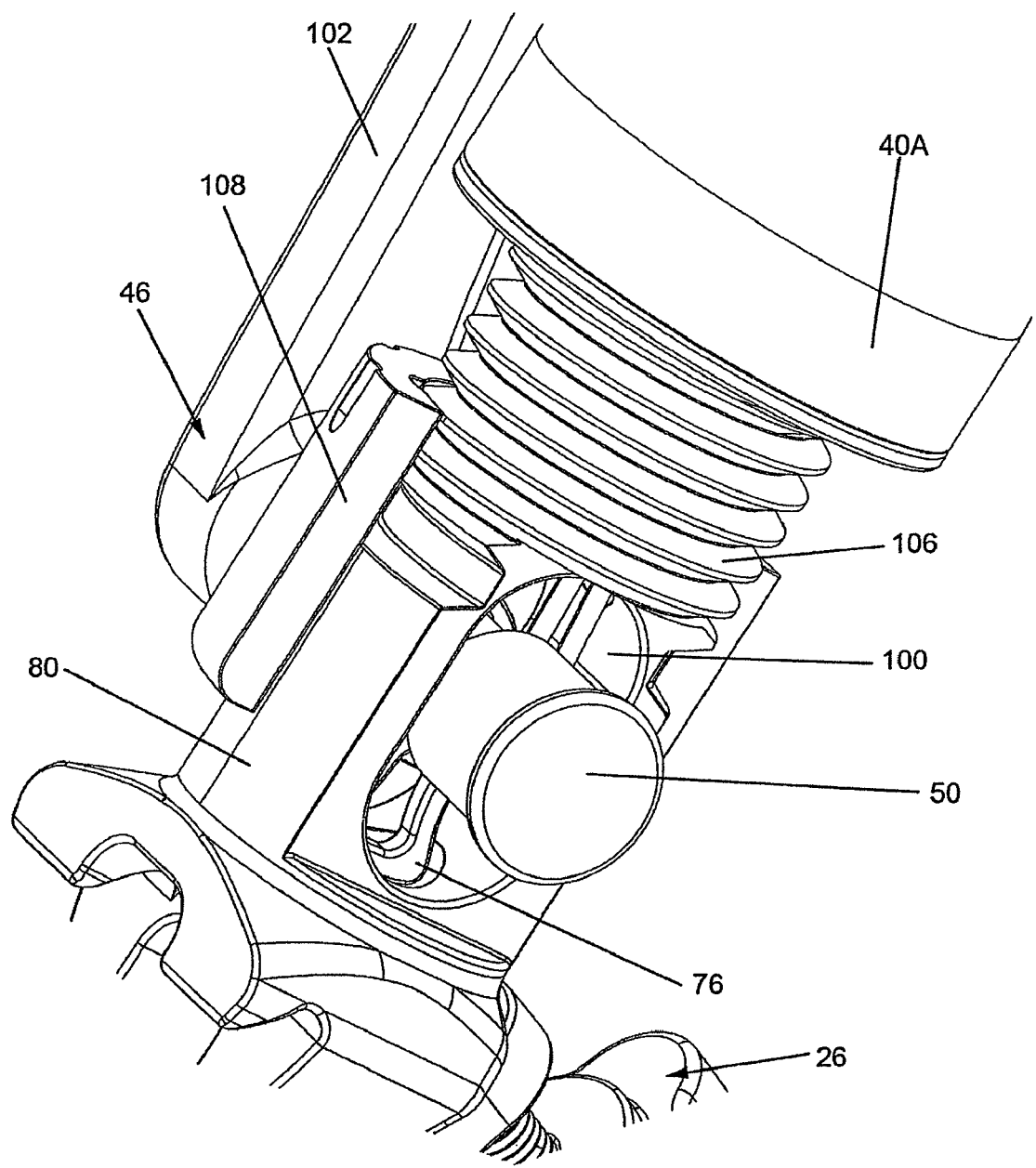
FIG. 9A is another isometric view (slightly enlarged in size as compared to FIG. 8) of a portion of the base assembly making up the positionable holding device of FIGS. 1 and 2, with other portions of the holding device not shown to reveal some of the interior details of the device.
Figure 9B:
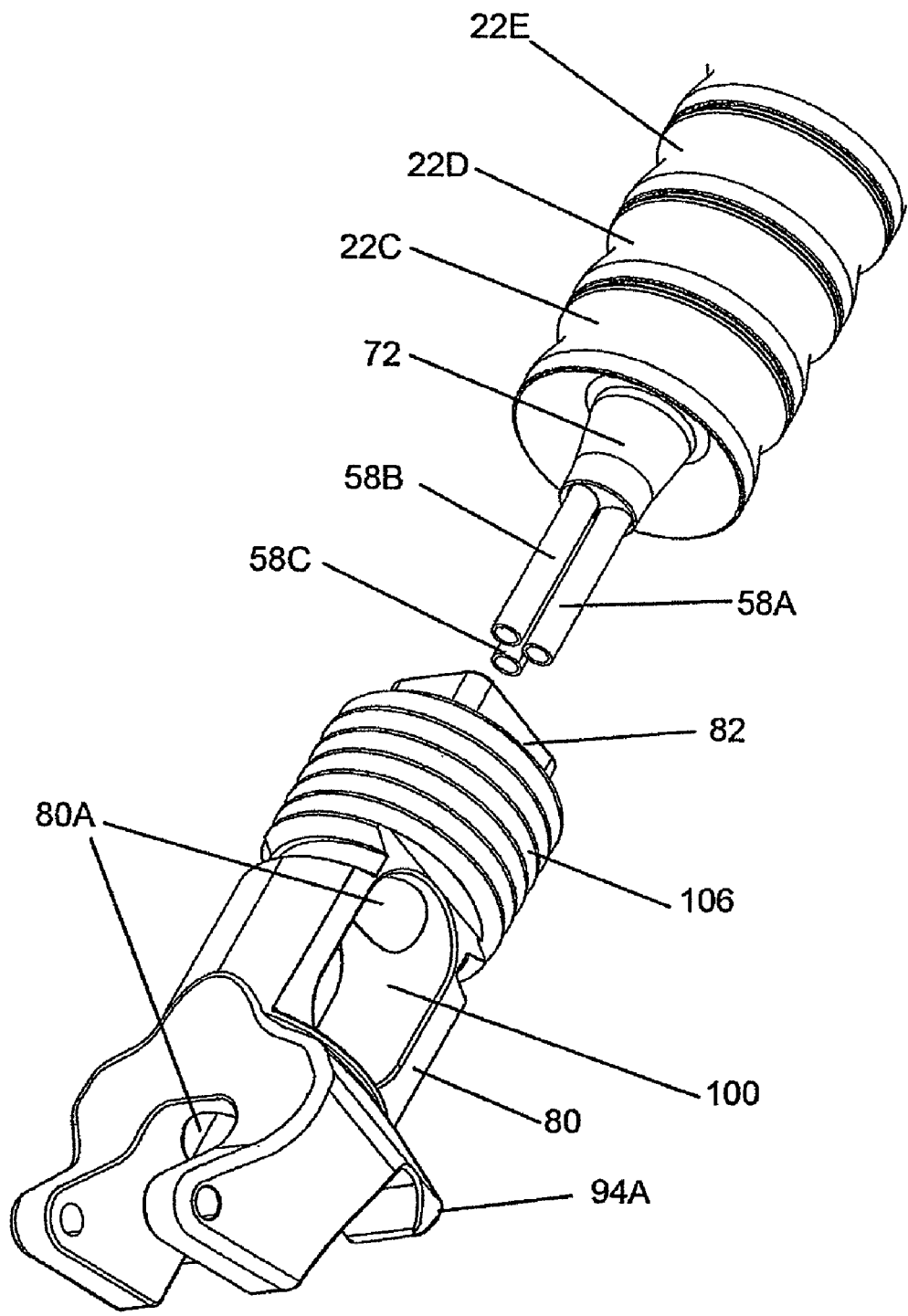
FIG. 9B is another isometric view (slightly reduced in size as compared to FIG. 8) of a portion of the base assembly making up the positionable holding device of FIGS. 1 and 2, with other portions of the holding device not shown to reveal some of the interior details of the device.

The base assembly 24 includes a secondary tensioning mechanism in the form of a threaded fine adjustment nut or collar 104. The threaded collar 104 (FIGS. 7 and 10) is threadedly engaged on a helical thread 106 extending about the distal portion of the housing member just beyond the slot 100. A split collar 108 (FIGS. 7, 8 and 9A) is located on the outer surface of the housing member 80. The split collar includes a pair of diametrically located openings in communication with respective ends of the slot 100 of the housing member 80 as best seen in FIG. 8. The proximal edge of the fine adjustment collar 104 extends over the distal peripheral edge of the split collar to hold the split collar along with the cam 50 and the lever 102 in place on the housing member 80. The fine adjustment collar 104 includes a detent (not shown) to prevent it from inadvertently loosening. The fine adjustment collar is arranged so that when it is tightened it pushes the cam shaft 50 of the tensioning assembly in the proximal direction (moves it downward) in the slot 100 thereby increasing the tension on the tensioning cable. As will be appreciated by those skilled in the art the tension in the cord 32 can be increased or decreased by rotating the collar 104 in the desired direction to move the cam shaft 50 closer or further from the pin 52 at the opposite end of the arm. This secondary tensioning mechanism enables the user to initially set the tension in the tensioning cord and to permit compensation for cord stretch over time, i.e., provide for user adjustability of the initial and ultimate tension of the tensioning band (ultimate holding power of the arm). User adjustment from unlocked to locked resistance to movement of the arm may be provided by other than the manually operated lever 102 just described. To that end, externally powered mechanisms, for example, a pneumatic or hydraulic cylinder may be used for tensioning and release.

While one preferred embodiment of the device 20 is made entirely of the non-magnetic and non-conductive materials described above, it is clear that the device 20 may be made so that it or some of its components is/are formed of materials that are magnetic resonance "safe" (non-magnetic), but do not fully meet the electrical non-conductivity criteria in parts of the device that are sufficiently remote from the imaging field that there is no detrimental effect to imaging. The arm itself has sufficient flexibility, strength, rigidity and ease of use in desired configurations and dimensions to meet required procedural demands.

Figure 6E:
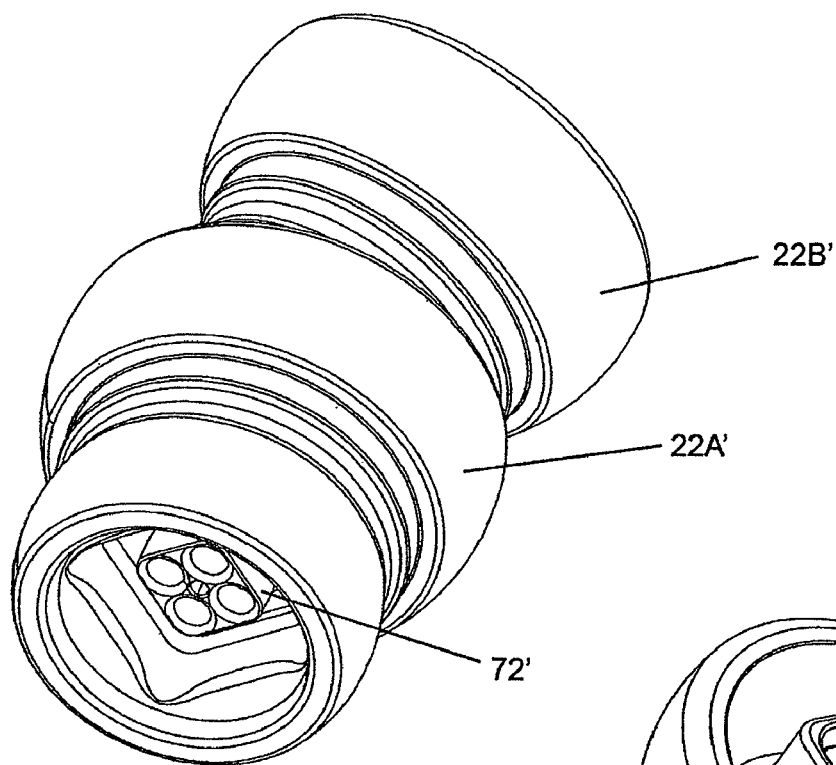
FIGS. 6E and 6F are respective isometric views of two contiguous segments of an arm constructed in accordance with an alternative embodiment of this invention.
Figure 6F:
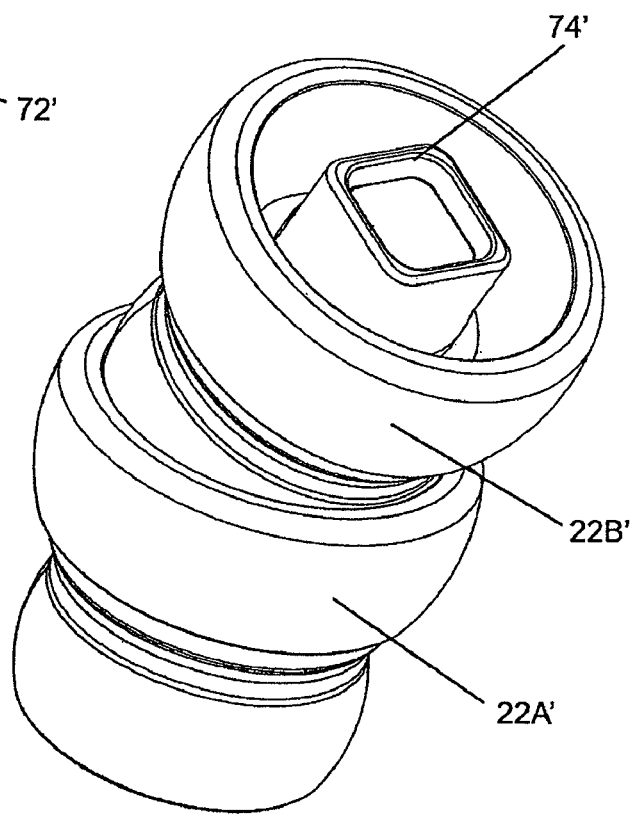

It should be pointed out at this juncture that the use of flexible tubes to prevent the segments twisting with respect to each other about the longitudinal axis of the arm is not the only way of accomplishing such action. Thus, it is contemplated that the segments can be constructed such that the projection of each segment has an external surface whose periphery is keyed to a corresponding shaped recess in the immediately adjacent segment to prevent the twisting of those segments with respect to each other. For example there is shown in FIGS. 6E and 6F two segments 22A' and 22B' of an arm so constructed. As can be seen therein each segment makes use of a square shaped projection 72' (FIG. 6E) and a corresponding square shaped recess 74' (FIG. 6F). Each segment has four apertures 72A', 72B', 72C' and 72D' through which four runs (not shown) of a tensioning cord pass. As will be appreciated by those skilled in the art, while the shape of each of the segments of this embodiment of the arm do offer the feature of preventing twisting they are more difficult to machine or mold than the segments 22A-22J of FIGS. 1 and 2. In addition with this embodiment one has to use a center line to hold the segments in close proximity to each other so that they don't loosen enough to let the joints separate and then reassemble with the tension cord runs twisted.

Figure 6G:
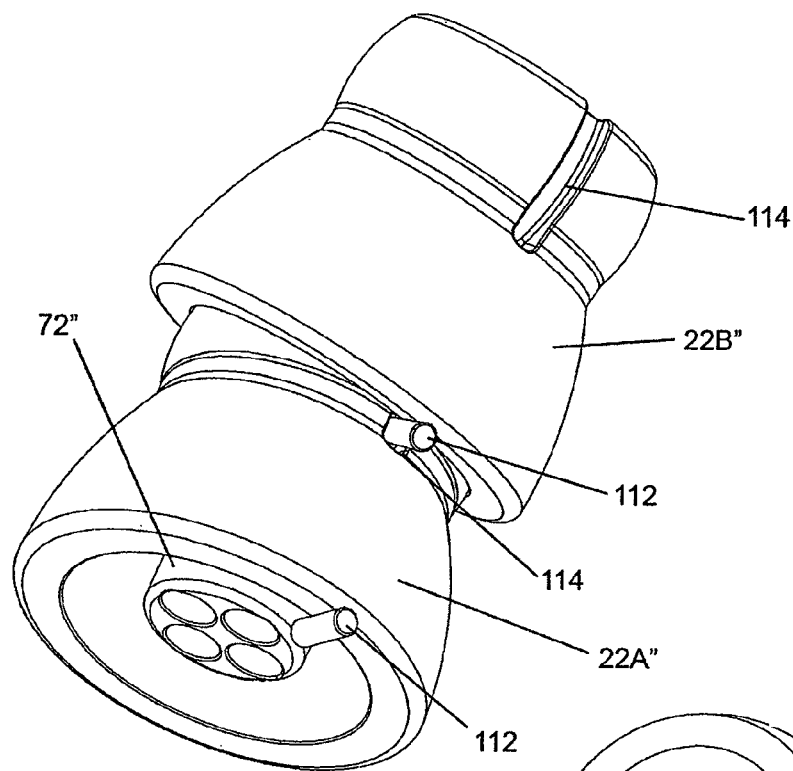
FIGS. 6G and 6H are respective isometric views of two contiguous segments of an arm construction in accordance with another alternative embodiment of this invention.
Figure 6H:
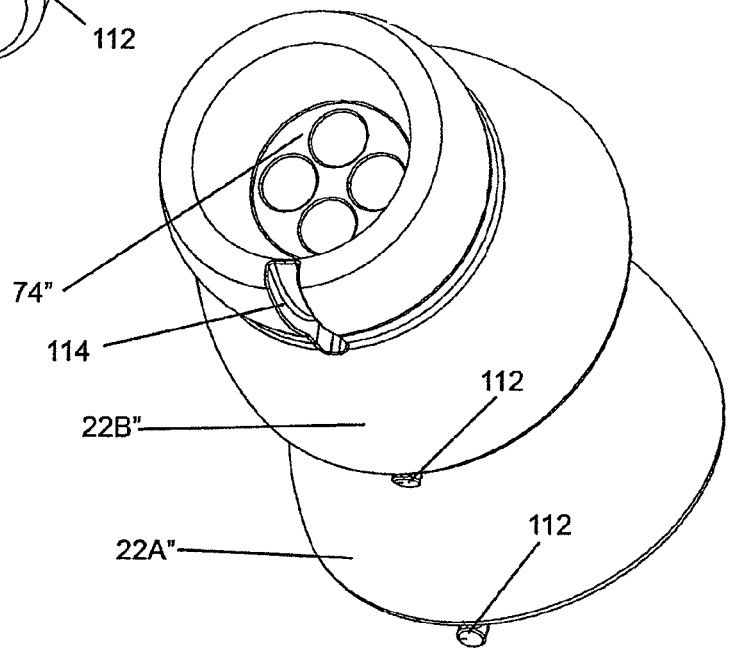

Another approach to preventing twisting of one segment of the arm with respect to its immediately adjacent segment is to key the segments via externally located keying means. For example there is shown in FIGS. 6G and 6H two segments 22A' and 22B' making use of an externally located pin 112 on the peripheral edge of the distal end portion of the segment and a corresponding groove 114 on the peripheral edge of the proximal end portion of the immediately adjacent segment.

It should be appreciated by those skilled in the art that the mass distribution and external shape of the arm segments is of considerable importance for ultimate strength and stability, and the internal shape is essential for the freedom of movement and consistent locking characteristics that allows adequate holding power and rigidity of the arm while preventing chafe of the tensioning band and movement of the arm during or after locking.

The size, shape and number of segments of the arm is a matter of choice dependent on the application for which the arm will be used. Although all the segments shown in the figures of the exemplary embodiment shown herein are very similar in dimension, it is contemplated, and indeed likely, that different size segments will be used in combination to achieve the optimal device for different applications. For example, to achieve a very stable arm with a small footprint in the operative field a tapered series of segments with larger segments at the base and progressively smaller segments proceeding to the free end could be used. Further still, the device's construction is modular so that its length, diameter, positioning possibilities and end effectors may be varied to meet specific requirements. Moreover, although manual locking and unlocking by tensioning and release of tension on the tensioning member is preferred, other forms of power and other mechanisms, such as a pneumatic or hydraulic rams could be used as well.

Figure 13:
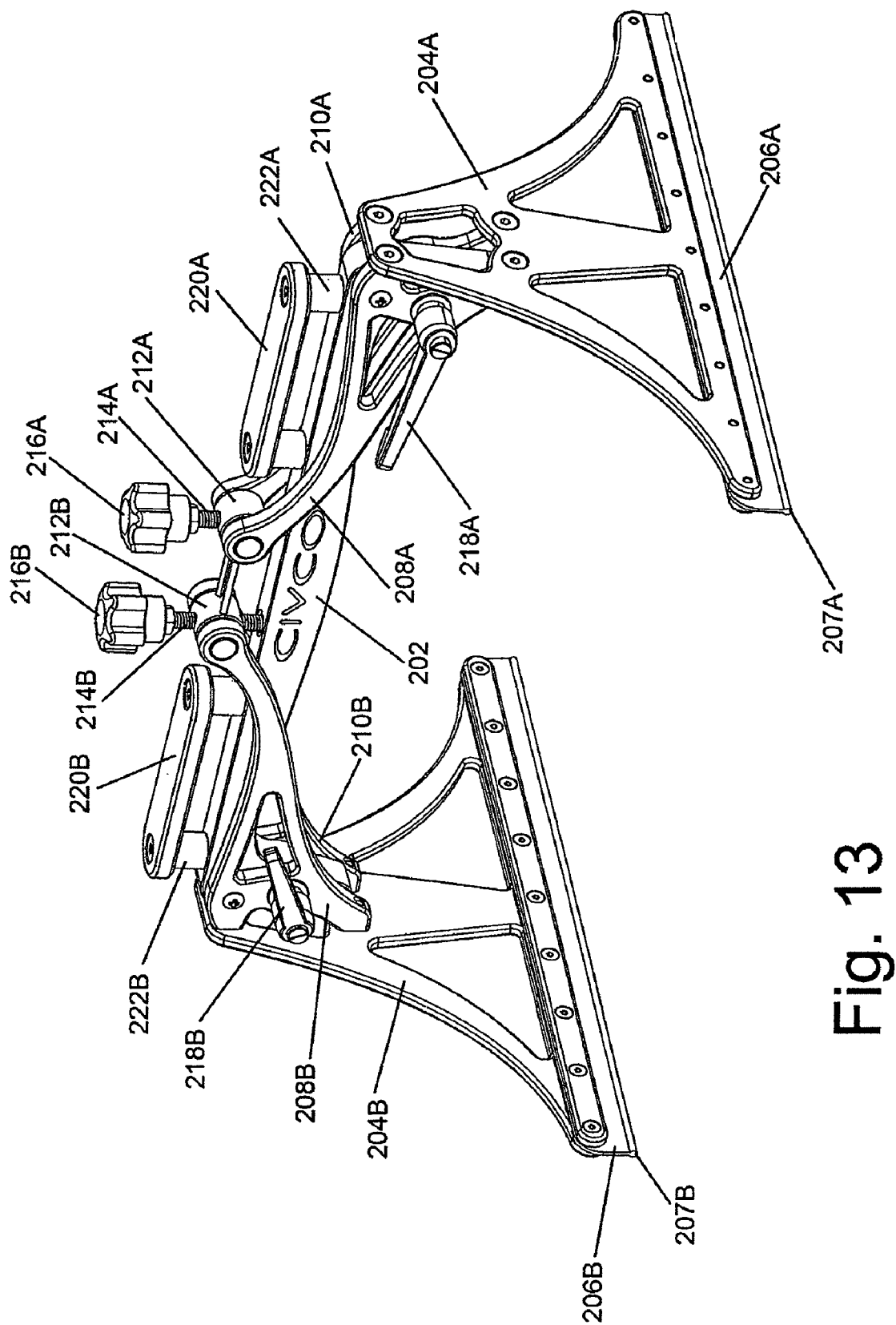
FIG. 13 is an isometric view of the adaptor device shown in FIG. 1 for mounting the positioning device on a patient support table like that of FIG. 1.
Figure 14:
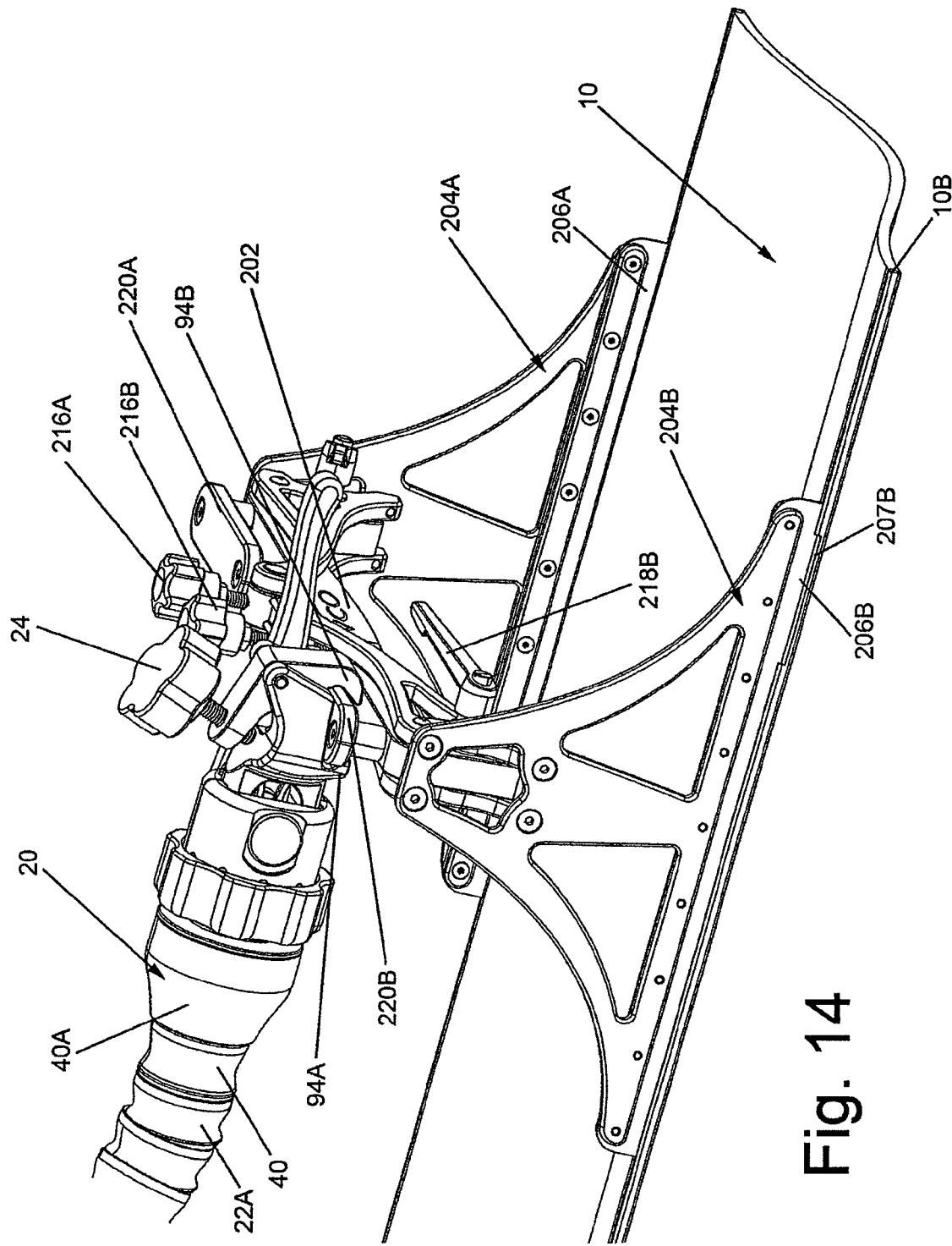
FIG. 14 is an isometric view of the proximal end portion of the positionable holding device of FIGS. 1-12, shown mounted on the adaptor device of FIG. 13 to mount the holding device at any desired longitudinal position on the patient support table.
Figure 15:
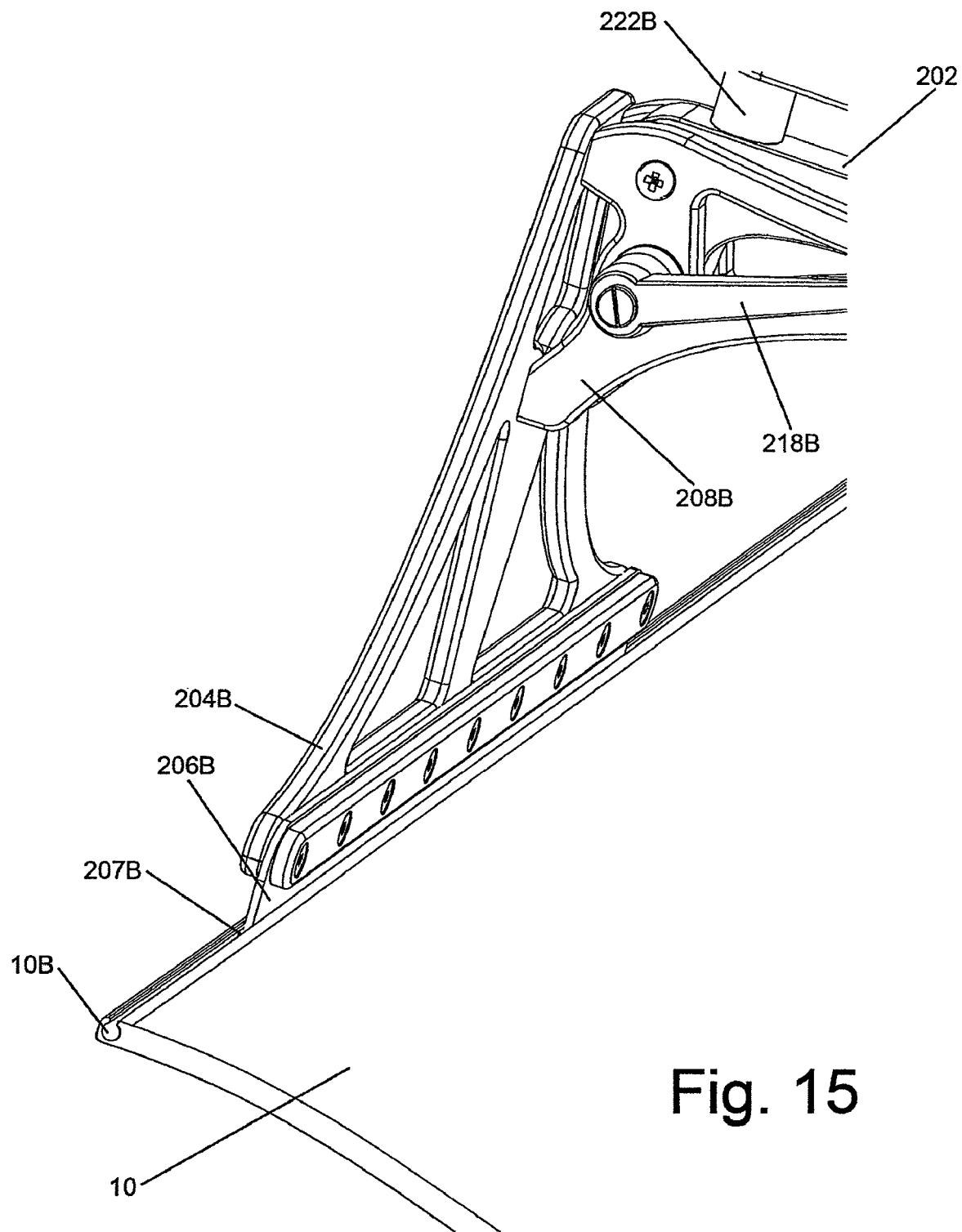
FIG. 15 is an enlarged isometric view of one portion of the adaptor device shown in FIGS. 13 and 14 for mounting it at any desired longitudinal position on the patient support table.

Referring now to FIGS. 1 and 13-15 the details of the adaptor 200 will now be described. As mentioned earlier the adaptor is a member that is constructed to enable a holding device, like device 20 constructed in accordance with this invention, to be mounted on a MRI scanner table that does not including a mounting rail or bar. It should be pointed out that the adaptor 200 can be used with other types of holding devices for MRI scanners, than the holding devices of this invention, providing that such other holding devices include a clamp structure for mounting such devices onto a rail or bar of a MRI table. In the embodiment shown in FIGS. 1 and 14 and 15 the table 10 does not include any rails or bars extending along its marginal edges to which the holding device 20 maybe releasably secured. It does, however, include a pair of undercut tracks 10A and 10B located in its top surface adjacent its marginal edges as best seen in FIGS. 14 and 15. The table 10, like the positioning device 20, is formed of a material that is MRI-safe. The adaptor 200 is also preferably formed of an MRI-safe material. Accordingly, neither the positioning device 20 nor the adaptor 200 or table 10 will interfere with the operation of the MRI scanner when they are is used to releasably mount and end effector 28 on the table 10.

The adaptor 200 basically comprises an elongated bridging member or cross piece 202 from which a pair of end plates or extensions 204A and 204B project downward. The end plates or extensions include lower edges in the form of respective rails which are arranged to be disposed within the undercut grooves or tracks 10A and 10B of the table 10. This arrangement enables the adaptor 200 to be slid along those tracks to any longitudinal position on the table and then locked in place at the desired longitudinal position. To that end, each of the extensions 204A and 204B is arranged to be pivoted inward slightly with respect to the cross piece 202 to tightly frictionally engage the track in which it is disposed to prevent accidental movement of the adaptor with respect to the table. In particular, the extension 204A is pivotably mounted on one end of the cross piece 202 by a pair of lever arms 208A and 210A, while the extension 204B is pivotably mounted on the other end of the cross piece by a pair of lever arms 208B and 210B. The inner end of each of the lever arms of the pair of lever arms 208A and 210A is pivotably mounted to one section 212A of a tension barrel nut, while the inner end of each of the lever arms of the pair of lever arms 208B and 210B is pivotably mounted to the other section 212B of the tension barrel nut. A pair of threaded screws 214A and 214B extend through respective threaded bores in the sections 212A and 212B, respectively, of the barrel nut and each terminates in a respective recess or bore in the top surface of the cross piece 202. The top end of the threaded screw 214A is in the form of a knob 216A, while the top end of the threaded screw 214B is in the form of a knob 216B.

The rotation of the knob 216A in the clockwise direction causes the section 212A of the barrel nut to move upward with respect to the cross piece 202, whereupon the inner end of lever arms 208A and 210A is pivoted upward, thereby causing the lower end of the associated end plate 204A to pivot inward. In a similar manner, the rotation of the knob 216B in the clockwise direction causes the section 212B of the barrel nut to move upward with respect to the cross piece 202, whereupon the inner end of lever arms 208B and 210B is pivoted upward, thereby causing the lower end of the associated end plate 204B to pivot inward.

Each of the end plates or extensions 204A and 204B is a generally planar member of a somewhat triangular frame shape. As best seen in FIGS. 13 and 15, the lower edge of each of the extensions 204A and 204B is in the form of a linear rail 206A and 206B, respectively. The lower edge of rail 206A is in the form of a bead 207A, while the lower edge of the rail 206B is in the form of a bead 207B. Each bead 207A and 207B is bulbous in cross section and is of a corresponding size and shape to the cross-sectional shape of the undercut tracks 10A and 10B, respectively, of the table 10. Thus, the lower edge of the extension 204A can be slidably disposed within the track 10A, while the lower edge of the other extension 204B can be slidably disposed within the other track 10B. When so mounted the adaptor 200 can be slidably located at any longitudinal position along the length of the table 10, with the bridging member or cross piece 202 spanning the width of the table. The knobs 216A and 216B be can then be operated as described above to releasably secure the adaptor at the desired position on the table.

In order to provide an extra measure of grip the adaptor includes a pair of tightening arms 218A and 218B coupled directly to lever arms 208A and 208B, respectively, indirectly coupled to lever arms 210A and 210B, respectively. The tightening arms cooperate with threaded screws (not shown) extending through the associated lever arms and the interposed cross piece 202 to fixedly secure the lever arms in their pivoted position after the extensions 204A and 204B have been pivoted inward by the desired amount of rotation of their adjusting knobs 216A and 216B, respectively. To that end, each of the tightening arms is in the form of a handle which adapted to be rotated to tighten its associated lever arms in place.

In order to mount the positioning device 20 on the adaptor 200, the adaptor includes a pair of horizontally oriented flat mounting bars 220A and 220B. These bars are disposed on pairs of respective stand-offs 222A and 222B on the top surface of the cross piece 202. In the embodiment shown in FIGS. 1 and 14 the positioning device 20 is mounted on the bar 220B on the left side of the adaptor. To that end, the jaws 94A and 94B of the base assembly 24 of the positioning device 20 are opened to receive that bar at any position along its length, i.e., a transverse position with respect to the table. The jaws of the positioning device are then closed to releasably mount the positioning device onto the left side of the adaptor 200 at the desired transverse position. The positioning device 20 can be mounted on the right side of the adaptor 200 in a similar manner.

While the positioning device has been described as being a manually controllable unit, it can, if desired, be constructed for automated positioning and operation. The foregoing is achieved by the use of available high technology materials that are electrically non-conductive and non-magnetic. These include strong and rigid polymer plastics and high strength, low stretch fibers. Moreover, the structure of its arm optimizes rigidity under load and avoids twisting of the central tensioning cord by preventing axial rotation of the supporting structural elements. This allows for the maintenance of constant length of the low stretch tensioning cord with manipulation and optimizes its tensioning capability, a feature that is of considerable importance for uniform movement and locking of the arm. The device's modular design elements facilitates easy assembly and provides versatility in choice of length and dimensional scalability of the segments that is critical to the arm's strength. The internal geometry of the segments of the arm and the use of the flexible sheaths for the cord runs allows bending of the arm without significantly changing the distance or relationship between supporting contact surfaces. This feature should provide viable long term use without degradation of the tensioning member. The device also includes a convenient and easy mechanism for the user to highly tension and then release that tension from the tensioning member during the fixation and subsequent release of the arm's position. The device is relatively compact, thereby enabling it to be made sterile by simply covering it with a sterile plastic sleeve and yet remains fully manipulable with the sleeve in place.

Without further elaboration the foregoing will so fully illustrate our invention that others may, by applying current or future knowledge, adopt the same for use under various conditions of service.

What is claimed is:

1. A device for holding an item adjacent an MRI apparatus, the MRI apparatus being used with a table, said device comprising an articulating arm having a proximal end portion and a free distal end portion and a flexible elongated tensioning member located within said arm between said proximal end portion and said distal end portion, said proximal end portion being in the form of a base arranged to mount said device on or at the MRI apparatus, said free distal end portion of said arm being arranged to mount a desired item thereon, said arm having a central longitudinal axis and comprising plural segments of non-magnetic and non-conductive material or any material that is at least one of magnetic resonance safe and artifact-free, each of said segments comprising a projection centered on said central longitudinal axis at least one of said segments having an arcuate concave socket and an immediately adjacent segment having an arcuate convex shoulder surface, said socket of said at least one of said segments receiving said arcuate convex shoulder surface of said immediately adjacent segment, each of said segments including a recess portion in said arcuate convex shoulder surface and a projection located in said socket, said projection of any one of said segments being located within the recess of the immediately adjacent segment, said elongated tensioning member being located internally within said arm and comprising a cord extending between said proximal and distal end portions of said arm, said cord being formed of a material that is at least one of magnetic resonance safe and artifact-free, said cord comprising plural sequentially connected runs, said runs extending through said projection of said segments parallel to each other and adjacent said central longitudinal axis, said segments being arranged to pivot with respect to each other but restricted from excess pivoting of said segment with respect to each other by the location of the projection of one segment within the recess of an immediately adjacent segment and also being restricted from twisting more than a predetermined angle with respect to each other about said longitudinal axis when said elongated tensioning member is un-tensioned to enable said arm to be moved or bent into a desired shape and held in such shape when said elongated tensioning member is tensioned.

2. The device of claim 1 wherein each of said segments has at least one aperture in it through which said elongated tensioning member extends.

3. The device of claim 1 wherein each of said segments has said arcuate concave socket and said arcuate convex shoulder surface.

4. The device of claim 1 wherein said tensioning member is actuatable to enable the tension in said elongated tensioning member to be established to hold said arm in said desired shape and to enable the tension in said elongated tensioning member to be released, whereupon the shape of said arm can be changed.

5. The device of claim 4 wherein said tensioning member extends about an offset surface located at said base, the orientation of said offset surface being adjustable to enable the adjustment of the tension on said tensioning member.

6. The device of claim 1 wherein said base includes a clamp for releasably securing said device to the table.

7. A device for holding an item adjacent an MRI apparatus, said device comprising an articulating arm having a proximal end portion and a free distal end portion and a flexible elongated tensioning member located within said arm between said proximal end portion and said distal end portion, said proximal end portion being in the form of a base arranged to mount said device on or at the MRI apparatus, said free distal end portion of said arm being arranged to mount a desired item thereon, said arm having a central longitudinal axis and comprising plural segments of non-magnetic and non-conductive material or any material that is at least one of magnetic resonance safe and artifact-free, each of said segments comprising a projection centered on said central longitudinal axis, said projection of each of said segments having an aperture in it located adjacent said central longitudinal axis through which said elongated tensioning member extends, said elongated tensioning member comprising a cord having at least two sequentially connected runs, each of said runs being disposed generally parallel to said longitudinal axis and extending through said apertures in said segments between said distal end portion and said proximal end portion, at least one of said segments having an arcuate concave socket and an immediately adjacent segment having an arcuate convex shoulder surface, said socket of said at least one of said segments receiving said shoulder surface of said immediately adjacent segment, said segments being arranged to pivot with respect to each other but restricted from twisting more than a predetermined angle with respect to each other about said longitudinal axis when said elongated tensioning member is un-tensioned to enable said arm to be moved or bent into a desired shape and held in such shape when said elongated tensioning member is tensioned.

8. The device of claim 7 wherein each of said segments has said arcuate concave socket and said arcuate convex shoulder.

9. The device of claim 7 wherein each of the segments includes a recess portion located in said convex shoulder surface and said projection located in said socket, said projection of any one of said segments being located within the recess of the immediately adjacent segment when said convex shoulder surface of said immediately adjacent segment is located within said socket of said any one of said segments to restrict excess pivoting of said segments with respect to one another.

10. The device of claim 9 wherein said aperture in each of said segments extends through said recess and said projection of said segment.

11. The device of claim 7 additionally comprising at least one sheath through which said cord extends, said sheath being fowled of a flexible material resistant to twisting.

12. The device of claim 11 additionally comprising plural sheaths formed of a flexible material resistant to twisting and extending through said segments and wherein said plural runs of said cord are disposed in respective ones of said plural sheaths.

13. The device of claim 7 wherein said tensioning member is actuatable to enable the tension in said elongated tensioning member to be established to hold said arm in said desired shape and to enable the tension in said elongated tensioning member to be released, whereupon the shape of said aim can be changed.

14. The device of claim 13 wherein said tensioning member extends about an offset surface located at said base, the orientation of said offset surface being adjustable to enable the adjustment of the tension on said tensioning member.

15. The device of claim 7 wherein said base includes a clamp for releasably securing said device to a table used with said MRI apparatus.

16. The device of claim 7 wherein said free end portion of said arm includes a clamp or releasably mounting an end effector thereon.

17. The device of claim 14 wherein the table includes at least one marginal edge said device includes an adaptor member arranged to be releasably mounted on the marginal edge of the table, said clamp of said device being arranged to be releasably secured to a portion of said adaptor member.

18. The device of claim 17 wherein the table includes a pair of marginal edges extending parallel to each other along respective sides of the table and wherein said adaptor member comprises a bridge member having a pair of extensions, each of which is arranged to slidingly engage a respective marginal edge of the table to releasably secure said adaptor at various positions along the table.

19. The device of claim 18 wherein each of the marginal edges of the table includes a respective one of a pair of recesses and wherein each of said extensions of said bridge member includes a free edge arranged to be disposed in a respective one of the recesses.

* * * * *